(12) United States Patent
Darien

(10) Patent No.: US 7,459,523 B2
(45) Date of Patent: Dec. 2, 2008

(54) EQUINE P-SELECTIN GLYCOPROTEIN LIGAND-1 AND USES THEREOF

(75) Inventor: Benjamin J. Darien, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/987,751

(22) Filed: Nov. 12, 2004

(65) Prior Publication Data

US 2005/0130206 A1    Jun. 16, 2005

Related U.S. Application Data

(60) Provisional application No. 60/519,418, filed on Nov. 12, 2003.

(51) Int. Cl.
*A61K 38/00* (2006.01)
*C07K 14/00* (2006.01)

(52) U.S. Cl. ............................... 530/300; 514/2; 514/12

(58) Field of Classification Search ........................ None
See application file for complete search history.

(56) References Cited

U.S. PATENT DOCUMENTS

| | | | |
|---|---|---|---|
| 6,124,267 | A | 9/2000 | McEver et al. |
| 6,277,975 | B1 | 8/2001 | Larsen et al. |
| 6,852,497 | B2 | 2/2005 | Lorenz et al. |
| 2002/0028205 | A1 | 3/2002 | Holgersson et al. |
| 2002/0037840 | A1 | 3/2002 | Lorenz et al. |
| 2002/0058034 | A1 | 5/2002 | Manjunath et al. |
| 2003/0049252 | A1 | 3/2003 | Lin et al. |
| 2004/0116333 | A1 | 6/2004 | Lin et al. |
| 2005/0152904 | A1 | 7/2005 | Lorenz et al. |

FOREIGN PATENT DOCUMENTS

| WO | WO98/08949 | 3/1998 |
|---|---|---|
| WO | WO 9808949 A1 * | 3/1998 |
| WO | WO99/43834 | 9/1999 |

OTHER PUBLICATIONS

Afshar-Kharghan V et al. (2001); Blood 97, 3306-3307.
Bundgaard J R et al. (1997); J Biol Chem 272, 21700-21705.
Cummings R D (1999); Brazilian Journal of Medical and Biological Research 32, 519-528.
Epperson T K et al. (2000); J Biol Chem 275, 7839-7853.
Hicks A E R et al. (2002); FASEB J 15, 1461-1462.
Lalko C C et al. (2003); Vet Immunology and Immunopathy 91, 119-134.
Leppänen A (2000); J Biol Chem 275, 39569-39578.
McEver R P et al. (1997); J Clin Invest 100, 485-492.
Moore K L (1998); Leukemia and Lymphoma 29, 1-15.
Rodgers S D et al. (2001); Biophys J 81, 2001-2009.
Snapp K R et al. (1998); J Cell Biol 142, 263-270.
Somers W S et al. (2000); Cell 103, 467-479.
Wilkins P P et al. (1996); J Biol Chem 271, 18732-18742.
Xia L et al. (2003); Blood 101, 552-559.
Veldman G et al. (1995); J Biol Chem 270, 16470-16475.
EMBL Sequence Version Archive Feb. 18, 2004; Accession No. AY298766.
Xu, J., et al. Mammalian Genome: Official Journal of the International Mammalian Genome Society 16:66-71 (Jan. 2005).
Darien, B.J. "Proceedings of a Workshop on Equine Immunology 2001" Havemeyar Foundation Monograph Series No. 4, pp. 91-93 (2001).

\* cited by examiner

*Primary Examiner*—Robert Landsman
*Assistant Examiner*—Ian Dang
(74) *Attorney, Agent, or Firm*—Quarles & Brady LLP

(57) ABSTRACT

A novel equine P-selectin glycoprotein ligand-1 (ePSGL-1) is disclosed having the amino acid sequence set forth in SEQ ID NO:2. DNA sequences encoding the ePSGL-1 are also disclosed, along with vectors, host cells, and methods of making the ePSGL-1. The invention further provides methods for preventing or reducing acute inflammatory response in an equine subject by administering ePSGL-1 and fragments thereof (e.g., an ePSGL-1-Ig fusion protein). The invention also provides methods for identifying compounds capable of reducing or preventing damage to tissue or organs caused by acute inflammatory response in an equine subject.

3 Claims, 11 Drawing Sheets

Fig. 1. (SEQ.ID NO:2)

```
CACTTCTCCT GGGCCCACGA GGCAGCTGTT CCATGCTCTG CTGAGCGCGG CACC                                              54
ATG CCT CTG CCG CTC CTC CTG CTG CTG AGC CTG CTG GGC CCT GGC AGC CGC CTC CAG CTT      114
Met Pro Leu Pro Leu Leu Leu Leu Leu Ser Leu Leu Gly Pro Gly Ser Arg Leu Gln Leu       20
GTC CGG GGC CAG ACA GGG GTG TCC AAG TAC TTA CAC AGA GAC GAC GTC AAC AGA GAA GGC      174
Val Arg Gly Gln Thr Gly Val Ser Lys Tyr Leu His Arg Asp Asp Val Asn Arg Glu Gly       40
ACG GAC CTG CTC AAA ACG CCT GAA AGC AGC ACC AAG ACT TTC TCC CTG AGC CCC AGG CTT      234
Thr Asp Leu Leu Lys Thr Pro Glu Ser Ser Thr Lys Thr Phe Ser Leu Ser Pro Arg Leu       60
CTG GAT GTG ATG GGG ACA CCA GAG CAG AGA GAT TCT ACA GGG CCT GGA ACT CCT GAG CCA      294
Leu Asp Val Met Gly Thr Pro Glu Gln Arg Asp Ser Thr Gly Pro Gly Thr Pro Glu Pro       80
GCC ACT CTG GAG GTG GCT ATG GAG GAC TCT GCT GGC CTG GGG GCA GGA GGG ACA GCC GTT      354
Ala Thr Leu Glu Val Ala Met Glu Asp Ser Ala Gly Leu Gly Ala Gly Gly Thr Ala Val      100
GGG AAC CTG ACC ACG GAA CTG GCC ACA CAG GGG ATT TCT GTC ACA ATG GGT CCT CTG ACC      414
Gly Asn Leu Thr Thr Glu Leu Ala Thr Gln Gly Ile Ser Val Thr Met Gly Pro Leu Thr      120
GAA GGA CTG GTC ACT ACA AAC CCT CCC TTC CTG GAG GCT CTA TCC ACA GAC GGG GCT CAG      474
Glu Gly Leu Val Thr Thr Asn Pro Pro Phe Leu Glu Ala Leu Ser Thr Asp Gly Ala Gln      140
TCC ACA GAG CTG GAT ACC CTG GAA GCC CTG TCC ACA GGA CCA GCA GCC ACG GAG GCA CTG      534
Ser Thr Glu Leu Asp Thr Leu Glu Ala Leu Ser Thr Gly Pro Ala Ala Thr Glu Ala Leu      160
ACC ACC CAA CCT GCA GCC ACG GAG GTC CTG TCC ACA GAA CCA GCA GCC ACG GAG GCA CTG      594
Thr Thr Gln Pro Ala Ala Thr Glu Val Leu Ser Thr Glu Pro Ala Ala Thr Glu Ala Leu      180
ACC ACC CAA CCC GCA GCC ACG GAG GTC CTG TCC ACG GAA CCA GCA GCC ACG GAG GCA CTG      654
Thr Thr Gln Pro Ala Ala Thr Glu Val Leu Ser Thr Glu Pro Ala Ala Thr Glu Ala Leu      200
ACC ACC CAA CCC GCA GCC ACA GAG GTC CTG TCC ACA GAA CCA GCA GCC ACG GAG GCA CTG      714
Thr Thr Gln Pro Ala Ala Thr Glu Val Leu Ser Thr Glu Pro Ala Ala Thr Glu Ala Leu      220
ACC TCC CAA CCC GCA GCC ACG GAG GTC TTG TCC AAA GGA CCA GCA GCC ACG GAG GCA CTG      774
Thr Ser Gln Pro Ala Ala Thr Glu Val Leu Ser Lys Gly Pro Ala Ala Thr Glu Ala Leu      240
ACC ACC CAA CCC GCA GCC ACA GAG GTC CTG TCC ACG GAA CCA GCA GCC ACG GAG GCA CTG      834
Thr Thr Gln Pro Ala Ala Thr Glu Val Leu Ser Thr Glu Pro Ala Ala Thr Glu Ala Leu      260
ACC TCC CAA CCT GCA GCC ACG GAG GTC TTG TCC AAA GGA CCA GCA GCC ACG GAG GCA CTG      894
Thr Ser Gln Pro Ala Ala Thr Glu Val Leu Ser Lys Gly Pro Ala Ala Thr Glu Ala Leu      280
ACC ACC CAA CCC GCA GTT ACG GAG GCC CAG TCC ACA GTT CTA GCC ACC ACC AGC TTC AGA      954
Thr Thr Gln Pro Ala Val Thr Glu Ala Gln Ser Thr Val Leu Ala Thr Thr Ser Phe Arg      300
GGA AAA AGC CAG ACT GTT TCC CTG TTG AGT TCT ACG GTC CCC AAC CCC ACA GTC GCC TGG     1014
Gly Lys Ser Gln Thr Val Ser Leu Leu Ser Ser Thr Val Pro Asn Pro Thr Val Ala Trp      320
GAC CAC ATC CCA GTG AAG CAG TGC CTG CTC GCC ATC CTT ATC CTC GCC CTG TTG GCT ACC     1074
Asp His Ile Pro Val Lys Gln Cys Leu Leu Ala Ile Leu Ile Leu Ala Leu Leu Ala Thr      340
ATC TTC CTT GTG TGC ACC GTG GTG CTG GCT GTC CGC CTC TCC CGC AAG AAC CAC ACA TAC     1134
Ile Phe Leu Val Cys Thr Val Val Leu Ala Val Arg Leu Ser Arg Lys Asn His Thr Tyr      360
CCC GTG CGC AGT TAC TCC CCC ACT GAC ATG GTT TGC ATC TCA TCC CTG CTG CCC GAG GGA     1194
Pro Val Arg Ser Tyr Ser Pro Thr Asp Met Val Cys Ile Ser Ser Leu Leu Pro Glu Gly      380
GGC GAG GGG CCC ACC ACC ACG GCC AAT GGG GGC CTG CCC ACC CCC AAG GGT CGG GGC CGA     1254
Gly Glu Gly Pro Thr Thr Thr Ala Asn Gly Gly Leu Pro Thr Pro Lys Gly Arg Gly Arg      400
AAG GCG GGG CCC GGC GAG GAC CAT GAC GGG GAC GAC CTC ACC CTG CAC AGC TTC CTC CCT     1314
Lys Ala Gly Pro Gly Glu Asp His Asp Gly Asp Asp Leu Thr Leu His Ser Phe Leu Pro      420
TAG                                                                                   1317
CTCCCCCAAC CCATCCTCCT GAGCAGGACC CTGCCTCCTC GCTCCCTCCG TGGCCCACCG                    1377
AGCCACCAGC CAGCATTCAG GCTCAATTCC ACAGGTCTGG GCTTCCTCGG AGCTCCCTGG                    1437
GGTTGGGCAC CCTCAGGACT GGGCCCCTGG CCACTGCCGC ACACGGGACT GAGAACAGGC                    1497
AGACCAGGCC TGGCACGCAG AGCTGCCCCC CGTCCTGACT CCAGTGGGGG CTGGCGACAC                    1557
TCCCTCCACC TCCCTGCCTC CCGTCTGTTC GGGGCGCCCT CCAGCACCCC CGCTGCTGTC                    1617
CTCCCCTCTC CTGGCTTCTG GGCCTCATTC GCGTGCACCC AGGGAGGACT CGGAGTCCCC                    1677
CGCCCTGACT CCCATTTTCT TCTGGTCGCC GTGGTCACCC ACAGGAAGGG GGCATTCAGG                    1737
AGGAGTGCTG GGCCCCGGAG GCCATGTCCT GCCGCTCCCC TATTTGGGGC AGCCTGGGTT                    1797
TTCTCGGCCG GCTCCCCAGG TCTCAGCCTG TGAGGACTGC GGCGAGTCTG GAGACCCCAC                    1857
GGCTGCCCCC TTCTTCGGGA CTGTGTGGAC CCACGAGGGC CATCTGCTGA CAGAGCAACC                    1917
CCCTCCTGCC CCCTCTTGCC TTCCCCCGGA GCCACGTTTC GGGGTGGGCT CTGTCTGGTT                    1977
CACAGAGCCA CCCCACTGCC CGGCCCATCC TCCGATGCAG CGCAGACACC CAATAAATAT                    2037
TGATGGTTGA CTNAAAAAAA AAAAAAAA                                                       2065
```

Fig. 2.

A. Signal peptide

```
1  MPLPLLLLLSLLGPGSRL        Horse PSGL-1 (SEQ.ID NO:14)
1  MPLQLLLLLILLGPGNSL        Human PSGL-1 (SEQ.ID NO:15)
```

B. Transmembrane domain

```
329  LLAILILALLATIFLVCTVVLAV  Horse PSGL-1 (SEQ.ID NO:16)
311  LLAILILALVATIFFVCTVVLAV  Human PSGL-1 (SEQ.ID NO:17)
```

C. Cytoplasmic domain

```
352  RLSRKNHTYPVRSYSPTEMVCISSL   Horse PSGL-1 (SEQ.ID NO:18)
334  RLSRKGHMYPVRNYSPTEMVCISSL   Human PSGL-1 (SEQ.ID NO:19)

377  LPEGGEGPTTTANGGLPTPKGRGRK   Horse PSGL-1 (SEQ.ID NO:20)
359  LPDGGEGPSATANGGLSKAKSPGLT   Human PSGL-1 (SEQ.ID NO:21)

402  AGPGEDHDGDDLTLHSFLP         Horse PSGL-1 (SEQ.ID NO:22)
384  PEPREDRGGDDLTLHSFLP         Human PSGL-1 (SEQ.ID NO:23)
```

Fig. 3.

A. Pattern of 10 residues repeats with consensus sequence: S/T-T-Q/E-P-A-A-T-E-A/V-L 151 STGPAATEAL (SEQ.ID NO:3)
    161 TTQPAATEVL (SEQ.ID NO:4)
    171 STEPAATEAL (SEQ.ID NO:5)
    181 TTQPAATEVL (SEQ.ID NO:4)
    191 STEPAATEAL (SEQ.ID NO:5)
    201 TTQPAATEVL (SEQ.ID NO:4)
    211 STEPAATEAL (SEQ.ID NO:5)
    221 TSQPAATEVL (SEQ.ID NO:6)
    231 SKGPAATEAL (SEQ.ID NO:7)
    241 TTQPAATEVL (SEQ.ID NO:4)
    251 STEPAATEAL (SEQ.ID NO:5)
    261 TSQPAATEVL (SEQ.ID NO:6)
    271 SKGPAATEAL (SEQ.ID NO:7)
    281 TTQPAVTEAQ (SEQ.ID NO:8)

B. Pattern of 20 residues repeats with consensus sequence:
S-T-E-P-A-A-T-E-A-L-T-T-Q-P-A-A-T-E-V-L 151 STGPAATEALTTQPAATEVL (SEQ.ID NO:9)
    171 STEPAATEALTTQPAATEVL (SEQ.ID NO:10)
    191 STEPAATEALTTQPAATEVL (SEQ.ID NO:10)
    211 STEPAATEALTSQPAATEVL (SEQ.ID NO:11)
    231 SKGPAATEALTTQPAATEVL (SEQ.ID NO:12)
    251 STEPAATEALTSQPAATEVL (SEQ.ID NO:11)
    271 SKGPAATEALTTQPAVTEAQ (SEQ.ID NO:13)

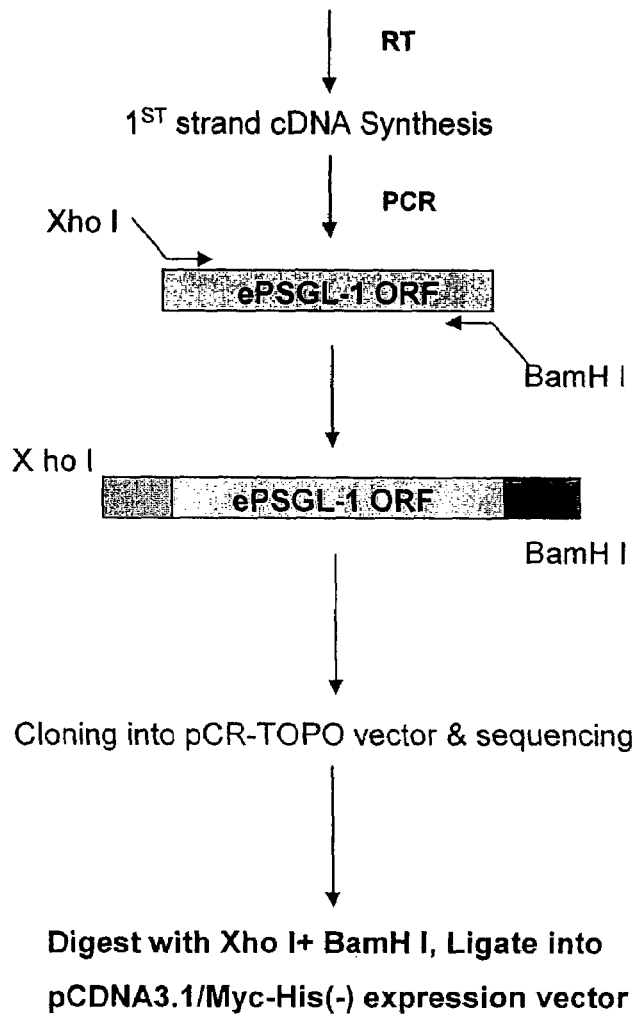
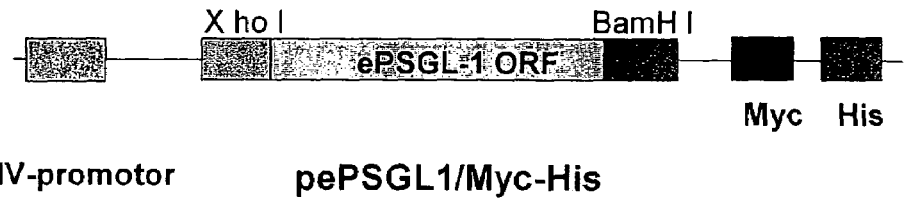
Fig. 4

SEQUENCE LISTING

```
<160> NUMBER OF SEQ ID NOS: 2

<210> SEQ ID NO 1
<211> LENGTH: 2065
<212> TYPE: DNA
<213> ORGANISM: Equus caballus
<220> FEATURE:
<221> NAME/KEY: misc_feature
<222> LOCATION: (2050)..(2050)
<223> OTHER INFORMATION: n is a, c, g, or t

<400> SEQUENCE: 1
cacttctcct gggcccacga ggcagctgtt ccatgctctg ctgagcgcgg caccatgcct      60
ctgccgctcc tcctgctgct gagcctgctg ggccctggca gccgcctcca gcttgtccgg     120
ggccagacag gggtgtccaa gtacttacac agagacgacg tcaacagaga aggcacggac     180
ctgctcaaaa cgcctgaaag cagcaccaag actttctccc tgagcccag gcttctggat      240 gtgatgggga caccagagca gagagattct acagggcctg gaactcctga gccagccact     300
ctggaggtgg ctatggagga ctctgctggc ctggggcag gagggacagc cgttgggaac      360
ctgaccacgg aactggccac acaggggatt tctgtcacaa tgggtcctct gaccgaagga     420
ctggtcacta caaaccctcc cttcctggag gctctatcca cagacgggc tcagtccaca      480 gagctggata ccctggaagc cctgtccaca ggaccagcag ccacggaggc actgaccacc     540
caacctgcag ccacggaggt cctgtccaca gaaccagcag ccacggaggc actgaccacc     600
caacccgcag ccacggaggt cctgtccacg gaaccagcag ccacggaggc actgaccacc     660
caacccgcag ccacagaggt cctgtccaca gaaccagcag ccacggaggc actgacctcc     720
caacccgcag ccacggaggt cttgtccaaa ggaccagcag ccacggaggc actgaccacc     780
caacccgcag ccacagaggt cctgtccacg gaaccagcag ccacggaggc actgacctcc     840
caacctgcag ccacggaggt cttgtccaaa ggaccagcag ccacggaggc actgaccacc     900
caacccgcag ttacggaggc ccagtccaca gttctagcca ccaccagctt cagaggaaaa     960
agccagactg tttccctgtt gagttctacg gtccccaacc ccacagtggc ctgggaccac   1020
atcccagtga agcagtgcct gctggccatc cttatcctgg ccctgttggc taccatcttc   1080
cttgtgtgca ccgtggtgct ggctgtccgc ctctcccgca gaaccacac ataccccgtg   1140
```

```
cgcagttact cccccactga gatggtttgc atctcatccc tgctgcccga gggaggcgag    1200
gggcccacca ccacggccaa tgggggcctg cccaccccca aggtcgggg ccgaaaggcg    1260 gggcccggcg aggaccatga cggggacgac ctcaccctgc acagcttcct cccttagctc    1320
ccccaaccat cctcctgagc aggaccctgc ctcctcgctc cctccgtggc ccaccgagcc    1380
accagccagc attcaggctc aattccacag gtctgggctt cctcggagct ccctggggtt    1440
gggcaccctc aggactgggc ccctggccac tgccgcacac gggactgaga acaggcagag    1500
caggcctggc acgcagagct gcccccgtc ctgactccag tgggggctgg cgagactccc    1560
tccacctccc tgcctcccgt ctgttcgggg cgccctccag caccccgct gctgtcctcc    1620 cctctcctgg cttctgggcc tcattcgcgt gcacccaggg aggactcgga gtaccccgc    1680 cctgactccc attttcttct ggtcgccgtg gtcacccaca ggaaggggc attcaggagg    1740 agtgctgggc cccggaggcc atgtcctgcc gctccctat ttggggcagc ctgggttttc    1800
tcgggcggct ccccaggtct cagcctgtga ggactgcggc gagtctggag accccagggc    1860
tgcccccttc ttcgggactg tgtggaccca cgagggccat ctgctgacag agcaaccccc    1920
tcctgccccc tcttgccttc ccccgcagcc acgtttcggg gtgggctctg tctggttcac    1980
agagccaccc cactgcccgg cccatcctcc gatgcagcgc agacacccaa taaatattga    2040
tggttgactn aaaaaaaaaa aaaaa                                          2065
```

<210> SEQ ID NO 2
<211> LENGTH: 420
<212> TYPE: PRT
<213> ORGANISM: Equus caballus

<400> SEQUENCE: 2

```
Met Pro Leu Pro Leu Leu Leu Leu Ser Leu Leu Gly Pro Gly Ser
1               5                   10                  15

Arg Leu Gln Leu Val Arg Gly Gln Thr Gly Val Ser Lys Tyr Leu His
            20                  25                  30

Arg Asp Asp Val Asn Arg Glu Gly Thr Asp Leu Leu Lys Thr Pro Glu
        35                  40                  45

Ser Ser Thr Lys Thr Phe Ser Leu Ser Pro Arg Leu Leu Asp Val Met
    50                  55                  60

Gly Thr Pro Glu Gln Arg Asp Ser Thr Gly Pro Gly Thr Pro Glu Pro
65                  70                  75                  80

Ala Thr Leu Glu Val Ala Met Glu Asp Ser Ala Gly Leu Gly Ala Gly
                85                  90                  95

Gly Thr Ala Val Gly Asn Leu Thr Thr Glu Leu Ala Thr Gln Gly Ile
            100                 105                 110

Ser Val Thr Met Gly Pro Leu Thr Glu Gly Leu Val Thr Asn Pro
            115                 120                 125

Pro Phe Leu Glu Ala Leu Ser Thr Asp Gly Ala Gln Ser Thr Glu Leu
    130                 135                 140

Asp Thr Leu Glu Ala Leu Ser Thr Gly Pro Ala Ala Thr Glu Ala Leu
145                 150                 155                 160

Thr Thr Gln Pro Ala Ala Thr Glu Val Leu Ser Thr Glu Pro Ala Ala
                165                 170                 175

Thr Glu Ala Leu Thr Thr Gln Pro Ala Ala Thr Glu Val Leu Ser Thr
            180                 185                 190

Glu Pro Ala Ala Thr Glu Ala Leu Thr Thr Gln Pro Ala Ala Thr Glu
        195                 200                 205
```

-continued

```
Val Leu Ser Thr Glu Pro Ala Ala Thr Glu Ala Leu Thr Ser Gln Pro
    210                 215                 220
Ala Ala Thr Glu Val Leu Ser Lys Gly Pro Ala Ala Thr Glu Ala Leu
225                 230                 235                 240
Thr Thr Gln Pro Ala Ala Thr Glu Val Leu Ser Thr Glu Pro Ala Ala
                245                 250                 255
Thr Glu Ala Leu Thr Ser Gln Pro Ala Ala Thr Glu Val Leu Ser Lys
            260                 265                 270

Gly Pro Ala Ala Thr Glu Ala Leu Thr Thr Gln Pro Ala Val Thr Glu
        275                 280                 285

Ala Gln Ser Thr Val Leu Ala Thr Thr Ser Phe Arg Gly Lys Ser Gln
    290                 295                 300
Thr Val Ser Leu Leu Ser Ser Thr Val Pro Asn Pro Thr Val Ala Trp
305                 310                 315                 320
Asp His Ile Pro Val Lys Gln Cys Leu Leu Ala Ile Leu Ile Leu Ala
                325                 330                 335
Leu Leu Ala Thr Ile Phe Leu Val Cys Thr Val Val Leu Ala Val Arg
            340                 345                 350

Leu Ser Arg Lys Asn His Thr Tyr Pro Val Arg Ser Tyr Ser Pro Thr
        355                 360                 365

Glu Met Val Cys Ile Ser Ser Leu Leu Pro Glu Gly Gly Glu Gly Pro
    370                 375                 380
Thr Thr Thr Ala Asn Gly Gly Leu Pro Thr Pro Lys Gly Arg Gly Arg
385                 390                 395                 400
Lys Ala Gly Pro Gly Glu Asp His Asp Gly Asp Asp Leu Thr Leu His
                405                 410                 415
Ser Phe Leu Pro
            420
```

EQUINE P-SELECTIN GLYCOPROTEIN LIGAND-1 AND USES THEREOF

CROSS-REFERENCE TO RELATED APPLICATION

This application claims the benefit of U.S. Provisional 60/519,418, filed Nov. 12, 2003, which is incorporated herein to the extent that it is not inconsistent with the disclosure herein.

STATEMENT REGARDING FEDERALLY SPONSORED RESEARCH

This invention was made with United States government support awarded by the following agency: USDA/CSREES 02-CRHR-0-6055. The United States has certain rights in this invention.

FIELD OF THE INVENTION

This invention relates generally to the field of veterinary medicine. More particularly, the present invention is directed to a novel equine P-selectin glycoprotein ligand-1 (ePSGL-1), nucleotides encoding the same, and therapeutic methods to treat equine subjects based on the novel molecules.

BACKGROUND OF THE INVENTION

Despite recent progress in understanding molecular aspects of endotoxemia and development of novel therapies, mortality remains high in horses with severe abdominal crises, such as intestinal ischemia, salmonellosis, and neonatal septicemia (Morris 1991; Welch et al. 1992). In these acute inflammatory diseases, the immune response is triggered with cytokines and inflammatory mediators being released, and platelets being activated either by endotoxin, released from gram negative bacteria, and/or the coagulation cascade (Weiss and Rashid 1998). Those events result in vascular injury and possibly thrombosis, which is the final and often fatal outcome of these disorders.

The initial step in the inflammatory reaction begins with the tethering and rolling of the circulating leukocytes on an activated endothelium (McEver and Cummings 1997). The rolling process is mediated by a family of $Ca^{2+}$-dependent proteins, the selectins. Those membrane-bound selectins are expressed within the vasculature, on the surface of endothelial cells (P- and E-selectin), leukocytes (L-selectin), and platelets (P-selectin). As members of the selectin family, they all contain a C-type carbohydrate recognition domain at their N-terminus which plays a crucial role in interacting with their ligand proteins. Human P-selectin mediates leukocyte adhesion via its natural ligand, P-selectin glycoprotein ligand-1 (hPSGL-1), which is located on the surface of a variety of leukocytes, including neutrophils, monocytes, eosinophils, and lymphocytes (Hicks et al. 2002). In humans, the interaction between platelet P-selectin and leukocyte PSGL-1 plays a central role in inflammatory and thrombotic mechanisms in ischemic conditions by regulating leukocyte trafficking through cell adhesion, platelet-leukocyte aggregate formation and tissue factor expression (Cummings 1999; Moore 1998). Those human disorders share comparable pathomorphological features with intestinal ischemia, colitis, and neonatal septicemia in the equine. Recently, the inventor discovered that a high proportion of circulating equine platelets are in a primed state with high baseline level of P-selectin expression and require minimal stimulation to form aggregates (Laiko et al. 2003). As a result of the high basal state of platelet P-selectin expression, it is reasonable to propose that horses are predisposed to inflammatory and thrombotic disorders during gram-negative septicemia and endotoxemia as a result of enhanced platelet-leukocyte interaction via equine PSGL-1 (ePSGL-1).

It can be appreciated that there exists a need in veterinary medicine for improved methods of treating equine subjects susceptible to or suffering from acute inflammatory responses and thrombotic disorders. Methods to universally combat inflammatory and thrombotic disorders are highly sought after and their discovery would be welcomed by equine owners and veterinarians alike.

SUMMARY OF THE INVENTION

The present invention provides various equine P-selectin glycoprotein ligand-1 (ePSGL-1) polypeptides based on the amino acid sequence set forth in FIG. 1 (SEQ ID NO:2). Nucleic acids encoding the ePSGL-1 polypeptides are also disclosed, along with vectors, host cells, and methods of making ePSGL-1 polypeptides and fusion proteins based thereon. In addition, the invention provides therapeutic methods of reducing or preventing acute inflammatory response by administration of ePSGL-1 polypeptides and related fusion proteins.

In a first embodiment, the present invention provides an isolated polypeptide comprising: (a) an ePSGL-1 amino acid sequence set forth in SEQ ID NO:2; (b) an amino acid sequence at least 85% identical to the ePSGL-1 amino acid sequence set forth in SEQ ID NO:2; (c) a fragment of the amino acid sequence set forth in SEQ ID NO:2 or a conservative variation thereof capable of binding equine P-selectin; or (d) an immunogenic fragment comprising at least 10 contiguous amino acid residues of the amino acid sequence set forth in SEQ ID NO:2.

Certain preferred polypeptides according to the invention include at least a portion of the extracellular domain of ePSGL-1 predicted to provide equine P-selectin binding capacity. Particularly preferred polypeptides include a fragment of amino acid sequence comprising at least 11 contiguous amino acid residues selected from amino acid residues 19-328 of SEQ ID NO:2 (i.e., the extracellular domain of ePSGL-1) or conservative variations thereof capable of binding equine P-selectin (e.g., the fragment of amino acid residues 19 to 43). Such polypeptides or conservative variations thereof may be further modified by sulfation, glycosylation, or both.

In certain embodiments, the invention is directed to recombinant ePSGL-1-immunoglobulin (ePSGL-1-Ig) fusion proteins comprising: (a) an amino acid sequence from the extracellular domain of ePSGL-1 or a conservative variation thereof capable of binding equine P-selectin; and (b) a heterologous amino acid sequence derived from an immunoglobulin. Recombinant ePSGL-1-Ig polypeptides according to the invention are useful as equine P-selectin antagonists and consequently effective in preventing or reducing acute inflammatory responses in equine subjects.

In yet other embodiments, the invention provides pharmaceutical compositions comprising: (a) a therapeutically effective amount of a polypeptide including ePSGL-1 amino acid sequence set forth in SEQ ID NO:2 capable of binding equine P-selectin or a conservative variation thereof; and (b) a pharmaceutically-acceptable carrier. In preferred embodiments, such pharmaceutical compositions comprise the recombinant ePSGL-1-Ig fusion polypeptides described and claimed herein.

In addition, the invention encompasses isolated nucleic acids comprising: (a) a nucleotide sequence encoding an ePSGL-1 polypeptide as set forth in SEQ ID NO:2; (b) a nucleotide sequence capable of hybridizing under stringent conditions to a nucleotide sequence-specified in (a); (c) a nucleotide sequence capable of hybridizing under stringent conditions to a nucleotide sequence-specified in (a) and further encoding a polypeptide capable of binding equine P-selectin; (d) a nucleotide sequence encoding a polypeptide fragment of SEQ ID NO:2 capable of binding equine P-selectin; (e) a nucleotide sequence complementary to the nucleotide sequences of (a)-(d); or (f) an RNA equivalent of (a)-(e). A particularly preferred nucleic acid according to the invention includes the open reading frame for ePSGL-1 as determined by the present inventor and set forth in SEQ ID NO:1 from nucleotide residues 55-1317.

As well, processes for producing an isolated equine P-selectin glycoprotein ligand-1 (ePSGL-1) polypeptide are provided by the invention. Such processes include steps of: (a) culturing a host cell containing an isolated nucleic acid encoding an ePSGL-1 polypeptide under conditions that allow expression of the ePSGL-1 polypeptide; and (b) purifying the ePSGL-1 polypeptide from the host cell. In preferred embodiments, the process further includes the step of modifying the ePSGL-1 polypeptide by sulfation, glycosylation, or both.

In yet another embodiment, the invention is directed to methods for preventing or reducing an acute inflammatory response in a subject, most preferably in an equine subject. The acute inflammatory response may, for example, be related to intestinal ischemia, salmonellosis, or septicemia. Such methods include the step of administering to a subject in need of treatment an effective amount of a composition comprising an equine P-selectin antagonist. A preferred equine P-selectin antagonist is a soluble ePSGL-1 polypeptide capable of binding equine P-selectin, as described and claimed herein. In more preferred embodiments, the polypeptide further comprises a heterologous sequence derived from an immunoglobulin and the P-selectin antagonist is an ePSGL-1-Ig fusion protein.

Finally, the invention provides methods of screening for a compound that modulates the activity of an ePSGL-1 polypeptide. Methods according to the invention include steps of: (a) combining an ePSGL-1 polypeptide with at least one test compound under conditions permissive for the activity of the polypeptide, (b) assessing the activity of the polypeptide in the presence of the test compound; and (c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

In certain embodiments, the method of screening identifies compounds that modulate the direct physical interaction between an ePSGL-1 polypeptide and equine P-selectin. In other embodiments, the method of screening identifies compounds capable of modulating the intracellular signaling activity of ePSGL-1.

Other objects, features and advantages of the present invention will become apparent after review of the specification, claims and drawings.

BRIEF DESCRIPTION OF THE DRAWINGS

FIG. 1. The cDNA (SEQ ID NO:1) and inferred amino acid sequence (SEQ ID NO:2) of equine PSGL-1 derived by RT-PCR: The arrow indicates the putative signal sequence cleavage site; the site of interaction between P-selectin and PSGL-1, based on the presence of Tyrosine and Threonine residues, is at approximately amino acid residue 19 to 43; potential N-linked glycosylation site is boxed; the 14 decameric repeats beginning at Serine 151 are underlined; and the putative transmembrane domain is double underlined.

FIG. 2. Alignment of the (A) Signal peptide, (B) Transmembrane domain, and (C) Cytoplasmic domain between the horse and human PSGL-1. The amino acids differing from the consensus sequence between the horse and human are boxed.

FIG. 3. Alignment of the equine PSGL-1 repeating unit. (A) Alignment of the equine PSGL-1 decameric tandem repeats. (B) Alignment of the equine PSGL-1 repeating unit of 20 amino acids instead of 10.

FIG. 4. Schematic depiction of the construction of an equine PSGL-1 plasmid, pePSGL1-Myc/His.

DETAILED DESCRIPTION OF THE INVENTION

I. In General

Figure 5:
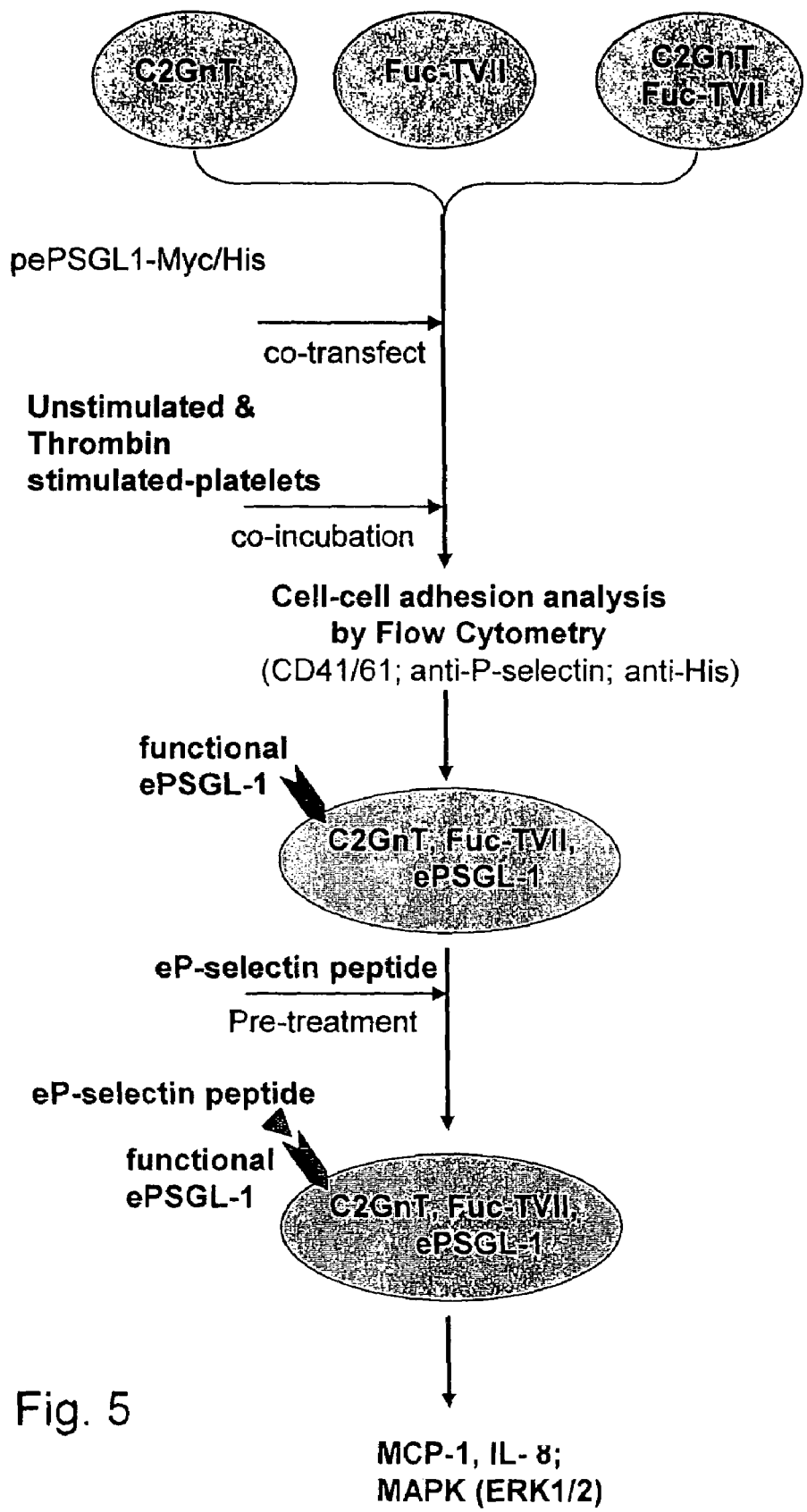
FIG. 5. Schematic illustration of establishment of a cell line expressing recombinant ePSGL-1 on the cell surface.

Before the present materials methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

II. The Invention

The present invention provides polypeptides, nucleic acids, compositions and methods for the modulation, e.g., prevention or reduction, of damage caused by acute inflammatory response in the equine subject. The term "equine subject" or "equine" shall encompass animals of the Equidae family including, but not limited to, horses, asses and zebras. Damage may be directed to a particular tissue or organ, as in intestinal ischemia. As well, damage may be systemic, such as the septicemia that all too commonly strikes equine neonates (i.e., neonatal septicemia). Accordingly, the present invention provides methods of administering an equine P-selectin antagonist, e.g., a soluble ePSGL-1, or a fragment thereof having ePSGL-1 activity, e.g., soluble ePSGL-1, or a soluble recombinant ePSGL-1 fusion protein, e.g., an ePSGL-1-Ig fusion protein. The equine P-selectin antagonist may be administered prior to or during an acute inflammatory response. In particularly preferred embodiments of the invention, the administration of soluble ePSGL-1 molecules to an equine subject prevents or reduces significantly the damage caused by acute abdominal crises in equine, namely, intestinal ischemia. Other preferred embodiments are directed to the administration of soluble ePSGL-1 molecules to an equine subject to prevent or reduce significantly the damage caused by a septicemic condition, particularly neonatal septicemia. In yet other embodiments, the invention provides administration of soluble ePSGL-1 molecules to an equine subject to prevent or reduce significantly the damage caused by salmonellosis.

As used herein, "ischemia" is any disorder or condition wherein blood flow is blocked or interrupted resulting in lack of blood supply and oxygen supply to any organ, tissue, or cells. Ischemia commonly occurs in the equine subject in an organ or tissue that is suffering a lack of oxygen supply. The ischemia is often due to a diseased or constricted intestine. Many medical interventions, such as the interruption of the flow of blood during surgery, for example, may lead to ischemia. Ischemia may also be caused by diseased cardiovascular tissue, and may affect cardiovascular tissue, such as in ischemic heart disease.

"Leukocyte rolling," as used herein, includes weak adhesion of leukocytes to endothelial cells of blood vessels and rolling of leukocytes along endothelial cells of blood vessels prior to firm adhesion cells and prior to transmigration of leukocytes into endothelial tissue. Following leukocyte rolling, these adherent leukocytes can migrate through the endothelium and destroy ischemic tissue during reperfusion. Accordingly, reduction of leukocyte rolling results in a reduction of damage to tissues and organs caused by acute inflammatory response.

The term "septicemia" as used herein refers to any systemic disorder or condition characterized by an acute inflammatory response due to a pathogenic organism or toxin thereof in the blood stream of an equine subject (e.g., neonatal septicemia).

As used herein, a "P-selectin antagonist" includes any agent which is capable of antagonizing P-selectin, e.g., by inhibiting interaction between P-selectin and a P-selectin ligand-1 protein, e.g., by inhibiting interaction of P-selectin expressing endothelial cells and activated platelets with PSGL expressing leukocytes. For example, P-selectin antagonists include ePSGL-1, or a fragment thereof having ePSGL-1 activity, e.g. soluble ePSGL-1, or a soluble recombinant ePSGL-1 fusion protein, e.g., recombinant ePSGL-1-Ig, as well as small molecules, anti-equine P-selectin antibodies, and anti-ePSGL-1 antibodies. In a preferred embodiment, the ePSGL-1 is soluble.

As used interchangeably herein, "equine P-selectin ligand-1 activity," "ePSGL-1 activity," "biological activity of ePSGL-1," or "functional activity of ePSGL-1 " includes an activity exerted by an ePSGL-1 protein, polypeptide or nucleic acid molecule on a ePSGL-1 responsive cell, e.g., platelet, leukocyte, or endothelial cell, as determined in vivo, or in vitro, according to standard techniques. ePSGL-1 activity can be a direct activity, such as an association with a ePSGL-1-target molecule, e.g., equine P-selectin. As used herein, a "substrate," or "target molecule," or "binding partner" is a molecule, e.g., equine P-selectin, with which an ePSGL-1 protein interacts, or binds to, in nature, such that ePSGL-1-mediated function, e.g., modulation of cell migration or adhesion, is achieved. An ePSGL-1 target molecule can be a non-ePSGL-1 molecule or an ePSGL-1 protein or polypeptide. Examples of such target molecules include proteins in the same signaling path as the ePSGL-1 protein, e.g., proteins which may function upstream (including both stimulators and inhibitors of activity) or downstream of the ePSGL-1 protein in a pathway involving regulation of equine P-selectin binding. Alternatively, an ePSGL-1 activity is an indirect activity, such as a cellular signaling activity mediated by interaction of the ePSGL-1 protein with an ePSGL-1 target molecule, e.g., equine P-selectin. The biological activities of ePSGL-1 are described herein, and include, for example, one or more of the following activities: 1) binding to or interacting with equine P-selectin; 2) modulating equine P-selectin binding; 3) modulating, e.g., decreasing or attenuating, cellular adhesion, e.g., intercellular adhesion (e.g., leukocyte-endothelial cell adhesion and leukocyte-platelet adhesion) and cell (e.g., leukocyte) adhesion to blood vessels; 4) modulating leukocyte recruitment to platelets and endothelial cells; 5) modulating cell (e.g., leukocyte or platelet) migration; 6) modulating, e.g., decreasing or attenuating, leukocyte rolling; 7) modulating, e.g., preventing or reducing, reperfusion injury following ischemia; and 8) modulating, e.g., preventing or reducing, the magnitude of infarcts following reperfusion.

As used herein, a "soluble ePSGL-1 protein," or a "soluble equine P-selectin glycoprotein ligand-1," refers to a soluble ePSGL-1 protein, e.g., soluble ePSGL-1, or a fragment thereof having an equine P-selectin ligand-1 activity. Proteins according to the invention preferably include at least a portion of the extracellular domain of ePSGL-1, i.e., a portion selected from the residues between amino acid 19 to about amino acid 328 of SEQ ID NO:2. Preferable proteins according to the invention are characterized as biologically active fragments of ePSGL-1. Soluble ePSGL-1 proteins (i.e., those absent transmembrane and cytoplasmic domain portions) used in the methods of the invention are preferably monomeric or dimeric ePSGL-1 proteins. In one embodiment of the methods of the invention, soluble forms of ePSGL-1 molecules of the invention may be fused through "linker" sequences to the Fc portion of an immunoglobulin, e.g., an IgG molecule, to form fusion proteins. Other immunoglobulin isotypes may also be used to generate such fusion proteins.

The methods of the invention further include the use of "allelic variants" of equine ePSGL-1, e.g., functional and non-functional allelic variants. "Functional allelic variants" are naturally occurring amino acid sequence variants of the equine ePSGL-1 protein that maintain an ePSGL-1 activity as described herein, e.g., P-selectin binding. Functional allelic variants will typically contain only conservative substitution of one or more amino acids of SEQ ID NO:2, or substitution, deletion or insertion of non-critical residues in non-critical regions of the protein. "Non-functional allelic variants" are naturally occurring amino acid sequence variants of the ePSGL-1 protein that do not have an ePSGL-1 activity. Non-functional allelic variants will typically contain a non-conservative substitution, deletion, or insertion or premature truncation of the amino acid sequence of SEQ ID NO:2, or a substitution, insertion or deletion in critical residues or critical regions of the protein.

Various aspects of the invention are described in further detail in the following subsections.

A. Isolated ePSGL-1 Proteins and Anti-ePSGL-1 Antibodies According to the Invention The present invention includes isolated ePSGL-1 proteins, e.g., ePSGL-1 proteins, and biologically active portions thereof, as well as polypeptide fragments suitable for use as immunogens to raise anti-ePSGL-1 antibodies. In one embodiment, native ePSGL-1 proteins can be isolated from cells or tissue sources by an appropriate purification scheme using standard protein purification techniques. In another embodiment, ePSGL-1 proteins are produced by recombinant DNA techniques. Alternative to recombinant expression, a ePSGL-1 protein or polypeptide can be synthesized chemically using standard peptide synthesis techniques.

As used herein, a "biologically active portion" or "biologically active fragment" of an ePSGL-1 protein includes a fragment of an ePSGL-1 protein having an ePSGL-1 activity. Biologically active portions of an ePSGL-1 protein include peptides comprising amino acid sequences sufficiently identical to or derived from the amino acid sequence of the ePSGL-1 protein, e.g., the amino acid sequence shown in SEQ ID NO:2, which include fewer amino acids than the full length ePSGL-1 proteins, and exhibit at least one activity of an ePSGL-1 protein. Typically, biologically active portions comprise a domain or motif with at least one activity of the ePSGL-1 protein (e.g., a fragment containing the extracellular domain of ePSGL-1, or a fragment thereof, which is capable of interacting with equine P-selectin). A biologically active portion of an ePSGL-1 protein can be a polypeptide which is, for example, 18, 20, 22, 25, 50, 75, 100, 125, 150, 175, 200, 250, 300, or more amino acids in length. Biologically active portions of an ePSGL-1 protein can be used as targets for developing agents which modulate ePSGL-1 activity.

In a preferred embodiment, the ePSGL-1 protein has at least an extracellular domain of the amino acid sequence shown in SEQ ID NO:2 or equine P-selectin binding fragment of the extracellular domain of ePSGL-1, or an extracellular domain of SEQ ID NO:2. In other embodiments, the ePSGL-1 protein is substantially identical to SEQ ID NO:2, and retains the functional activity of the protein of SEQ ID NO:2, yet differs in amino acid sequence due to natural allelic variation or mutagenesis, as described in detail herein. Accordingly, in another embodiment, the ePSGL-1 protein used in the methods of the invention is a protein which comprises an amino acid sequence at least about 85%, 90%, 91%, 92%, 93%, 94%, 95%, 96%, 97%, 98%, 99% or more identical to SEQ ID NO:2. In yet more preferred embodiments, the ePSGL-1 protein used in the methods represents a soluble form of ePSGL-1 (i.e., absent transmembrane and cytoplasmic domains) which comprises an amino acid sequence at least about 85%, 90%, 91%, 92%, 93%, 94%, 95%, 96%, 97%, 98%, 99% or more identical to SEQ ID NO:2 from amino acid 19 to 328 (i.e., the mature extracellular domain).

Thusly, certain ePSGL-1 proteins according to the invention are soluble ePSGL-1 molecules. A DNA encoding a soluble form of the ePSGL-1 may be prepared by expression of a modified DNA in which the regions encoding the transmembrane and cytoplasmic domains of the ePSGL-1 are deleted and/or a stop codon is introduced 3' to the codon for the amino acid at the carboxy terminus of the extracellular domain. For example, hydrophobicity analysis predicts that the P-selectin ligand-1 protein set forth in SEQ ID NO:2 has a transmembrane domain comprised of amino acids 329 to 351 of SEQ ID NO:2 and a cytoplasmic domain comprised of amino acids 352 to 420 of SEQ ID NO:2. A modified DNA as described above may be made by standard molecular biology techniques, including site-directed mutagenesis methods which are known in the art or by the polymerase chain reaction using appropriate oligonucleotide primers.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the ePSGL-1 amino acid sequence of SEQ ID NO:2 having 420 amino acid residues, preferably at least 336, and even more preferably at least 378 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. 48:444-453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (Comput. Appl. Biosci. 4:11-17 (1988)) which has been incorporated into the ALIGN program (version 2.0 or 2.0U), using a PAM120 weight residue table, a gap length penalty of 12 and a gap penalty of 4.

The methods of the invention may also use ePSGL-1 chimeric or fusion proteins. As used herein, an ePSGL-1 "chimeric protein" or "fusion protein" comprises an ePSGL-1 polypeptide operatively linked to a non-ePSGL-1 polypeptide. An "ePSGL-1 polypeptide" refers to a polypeptide having an amino acid sequence corresponding to an ePSGL-1 molecule, whereas a "non-ePSGL-1 polypeptide" (also termed "heterologous polypeptide" or "heterologous sequence") refers to a polypeptide having an amino acid sequence corresponding to a protein which is not substantially homologous to the ePSGL-1 protein, e.g., a protein which is different from the ePSGL-1 protein and which is derived from the same or a different organism. Within an ePSGL-1 fusion protein the ePSGL-1 polypeptide can correspond to all or a portion of an ePSGL-1 protein. In a preferred embodiment, an ePSGL-1 fusion protein comprises at least one biologically active portion of an ePSGL-1 protein, e.g., an extracellular domain of ePSGL-1 or equine P-selectin binding fragment thereof. In another preferred embodiment, an ePSGL-1 fusion protein comprises at least two biologically active portions of an ePSGL-1 protein. Within the fusion protein, the term "operatively linked" is intended to indicate that the ePSGL-1 polypeptide and the non-ePSGL-1 polypeptide are fused in-frame to each other. The non-ePSGL-1 polypeptide can be fused to the N-terminus or C-terminus of the ePSGL-1 polypeptide.

For example, in one embodiment, the fusion protein is a recombinant soluble form of ePSGL-1 protein in which a portion of the extracellular domain of the ePSGL-1 molecule is fused to equine IgG, e.g., soluble rPSGL-Ig. Preferred fusion proteins include at least the following ePSGL-1 amino acid residues from SEQ ID NO:2 and are of particular utility in constructing eSPGL-1-Ig fusion proteins: amino acid residues 30-41; amino acid residues 25-41; amino acid residues 28-46; amino acid residues 28-127; amino acid residues 28-150; and amino acid residues 19-328. Even more preferred contiguous residues from the extracellular domain are: amino acid residues 19-43; amino acid 19-60; amino acid residues 19-105; and amino acid residues 19-132. It should be further realized that conservative variations of these sequences are also within the scope of the invention. Other contiguous amino acid residues may certainly be selected and one of skill, after reading the disclosure provided herein, may construct equivalent fusion proteins of varying composition. In general, the selection of extracellular sequences is based on the inventor's characterization of the ePSGL-1 polypeptide and to how that equine version compares to known sequences, particularly human PSGL-1. Based on the inventor's analyses, a polypeptide. "capable of binding equine P-selectin" will include at least amino acid residues 30-41 as set forth in SEQ ID NO:2, or conservative variations thereof.

Because of the importance of post-translational modifications in non-equus PSGL/P-selectin binding, it is further envisioned that the recombinant ePSGL-1-Ig polypeptides described and claimed herein may be expressed in host cell lines capable of appropriate post-translational modifications. In particular, appropriate cell lines are capable of glycosylation and/or sulfation of the ePSGL-1 polypeptides. A particularly-preferred cell line for expression of ePSGL polypeptides is the CHO(C2GnT+Fuc-TVII) cell line described further in Example 3, capable of both glycosylation and sulfation of the ePSGL-1 polypeptide. Other suitable host cells include, but are not limted to, COS cells, K562 cells, and 293 kidney cells. Posttranslational modifications include tyrosine O-sulfation, sialylation modified with sialytransferase, fucosylation by addition of fucose in a α1-3 linkage with FucT-VII (α1-3 fucosyltransferase VII) directing the expression of sLex determinant exclusively, and branching of O-linked carbohydrates with C2GnT (core 2 β1-6-N-acetylglucosaminyl-transferase), and some of the specific enzymes that mediate these modifications. CHO cells are and excellent cell line for analyzing the effects of glycosylation on protein structure and function because they have well characterized oligosaccharide biosynthetic pathways. CHO cells synthesize O-glycans with simple core 1 structures, but have no endogenous α1-3 fucosyltransferase which direct the expression of sLex determinant and C2GnT activity which direct the formation of the core 2 structure. Similarly, COS cells are absent an endogenous α1-3 fucosyltransferase and C2GnT activity. The K562 hematopoietic cell line provides an excellent model system to study interactions of hematopoietic cells with both P- and E-selectin, since they do not endogenously express L-selectin, PSGL-1, or FucT-VII. 293 kidney cells presumably express endogeous C2GnT, since it is known that only co-expression of a α1-3 fucosyltransferase with PSGL-1 is needed for recognition by P-selectin.

The soluble ePSGL-1 fusion proteins used in the methods of the invention, e.g., rPSGL-Ig, can be incorporated into pharmaceutical compositions and administered to a equine subject in vivo. Accordingly, soluble ePSGL-1 proteins can be used to affect the bioavailability of an ePSGL-1 substrate, e.g., equine P-selectin. Consequently, acute inflammatory response, particularly the mechanisms of tethering and rolling of leukocytes to endothelial cells, can be reduced or prevented and a beneficial therapy realized for the animal subject.

In addition, the ePSGL-1-fusion proteins of the invention can be used as immunogens to produce anti-ePSGL-1 antibodies in a subject, to purify ePSGL-1 and in screening assays to identify molecules which inhibit the interaction of an ePSGL-1 molecule with an equine P-selectin molecule.

Preferably, an ePSGL-1 chimeric or fusion protein used in the methods of the invention is produced by standard recombinant DNA techniques. For example, DNA fragments coding for the different polypeptide sequences are ligated together in-frame in accordance with conventional techniques, for example, by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). An ePSGL-1-encoding nucleic acid can be cloned into such an expression vector such that the fusion moiety is linked in-frame to the ePSGL-1 protein.

The present invention also pertains to variants of the ePSGL-1 proteins which function as either ePSGL-1 agonists (mimetics) or as ePSGL-1 antagonists. Variants of the ePSGL-1 proteins can be generated by mutagenesis, e.g., discrete point mutation or truncation of an ePSGL-1 protein. An agonist of the ePSGL-1 proteins can retain substantially the same, or a subset of, the biological activities of the naturally occurring form of an ePSGL-1. An antagonist of an ePSGL-1 protein can inhibit one or more of the activities of the naturally occurring form of the ePSGL-1 protein by, for example, competitively modulating an ePSGL-1-mediated activity of an ePSGL-1 protein. Thus, specific biological effects can be elicited by treatment with a variant of limited function. In one embodiment, treatment of an equine subject with a variant having a subset of the biological activities of the naturally occurring form of the protein has fewer side effects in a subject relative to treatment with the naturally occurring form of the ePSGL-1 protein.

In one embodiment, variants of an ePSGL-1 protein which function as either ePSGL-1 agonists (mimetics) or as ePSGL-1 antagonists can be identified by screening combinatorial libraries of mutants, e.g., truncation mutants, of an ePSGL-1 protein for ePSGL-1 protein agonist or antagonist activity. In one embodiment, a variegated library of ePSGL-1 variants is generated by combinatorial mutagenesis at the nucleic acid level and is encoded by a variegated gene library. A variegated library of ePSGL-1 variants can be produced by, for example, enzymatically ligating a mixture of synthetic oligonucleotides into gene sequences such that a degenerate set of potential ePSGL-1 sequences is expressible as individual polypeptides, or alternatively, as a set of larger fusion proteins (e.g., for phage display) containing the set of ePSGL-1 sequences therein. There are a variety of methods which can be used to produce libraries of potential ePSGL-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential ePSGL-1 sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of an ePSGL-1 protein coding sequence can be used to generate a variegated population of ePSGL-1 fragments for screening and subsequent selection of variants of an ePSGL-1 protein. In one embodiment, a library of coding sequence fragments can be generated by treating a double stranded PCR fragment of a ePSGL-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal, C-terminal, and internal fragments of various sizes of the ePSGL-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of ePSGL-1 proteins. The most widely used techniques for screening large gene libraries, which are amenable to high through-put analysis, typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify ePSGL-1 variants (Arkin and Yourvan (1992) Proc. Natl. Acad. Sci. USA 89:7811-7815; Delgrave et al. (1993) Protein Engineering 6(3):327-331).

The present invention further encompasses anti-ePSGL-1 antibodies. An isolated ePSGL-1 protein, or a portion or fragment thereof, can be used as an immunogen to generate antibodies that bind ePSGL-1 using standard techniques for polyclonal and monoclonal antibody preparation.

A full-length ePSGL-1 protein or equine P-selectin protein can be used or, alternatively, antigenic peptide fragments of ePSGL-1 or equine P-selectin can be used as immunogens (Johnston et al. (1989) Cell 56:1033-1044). The antigenic peptide of ePSGL-1 comprises at least 8 amino acid residues of the amino acid sequence shown in SEQ-ID NO:2 and encompasses an epitope of ePSGL-1 such that an antibody raised against the peptide forms a specific immune complex with the ePSGL-1 protein. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of ePSGL-1 that are located on the surface of the protein, e.g., hydrophilic regions, as well as regions with high antigenicity.

An ePSGL-1 immunogen is typically used to prepare antibodies by immunizing a suitable subject, (e.g., rabbit, goat, mouse, or other mammal) with the immunogen. An appropriate immunogenic preparation can contain, for example, recombinantly expressed ePSGL-1 protein or a chemically synthesized ePSGL-1 polypeptide. The preparation can further include an adjuvant, such as Freund's complete or incomplete adjuvant, or similar immunostimulatory agent. Immunization of a suitable subject with an immunogenic ePSGL-1 preparation induces a polyclonal anti-ePSGL-1 antibody response.

The term "antibody" as used herein refers to immunoglobulin molecules and immunologically active portions of immunoglobulin molecules, i.e., molecules that contain an antigen binding site which specifically binds (immunoreacts with) an antigen, such as an ePSGL-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind ePSGL-1 molecules. The term "monoclonal antibody" or "monoclonal antibody composition", as used herein, refers to a population of antibody molecules that contain only one species of an antigen binding site capable of immunoreacting with a particular epitope of ePSGL-1. A monoclonal antibody composition thus typically displays a single binding affinity for a particular ePSGL-1 protein or equine P-selectin with which it immunoreacts.

Polyclonal anti-ePSGL-1 antibodies can be prepared as described above by immunizing a suitable subject with an ePSGL-1 or equine P-selectin immunogen. The anti-ePSGL-1 antibody titer in the immunized subject can be monitored over time by standard techniques, such as with an enzyme linked immunosorbent assay (ELISA) using immobilized equine P-selectin. If desired, the antibody molecules directed against either antigen can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) Nature 256:495-497) (see also, Brown et al. (1981) J. Immunol. 127:539-46; Brown et al. (1980) J. Biol. Chem. 255:4980-83; Yeh et al. (1976) Proc. Natl. Acad. Sci. USA 76:2927-31; and Yeh et al, (1982) Int. J. Cancer 29:269-75), the more recent human B cell hybridoma technique (Kozbor et al. (1983) Immunol Today 4:72), the EBV-hybridoma technique (Cole et al. (1985) Monoclonal Antibodies and Cancer Therapy, Alan R. Liss, Inc., pp. 77-96) or trioma techniques. The technology for producing monoclonal antibody hybridomas is well known (see generally Kenneth, R. H. in Monoclonal Antibodies: A New Dimension In Biological Analyses, Plenum Publishing Corp., New York, N.Y. (1980); Lerner, E. A. (1981) Yale J. Biol. Med. 54:387-402; Gefter, M. L. et al. (1977) Somatic Cell Genet. 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds ePSGL-1.

Any of the many well known protocols used for fusing lymphocytes and immortalized cell lines can be applied for the purpose of generating an anti-ePSGL-1 monoclonal antibody (see, e.g., G. Galfre et al. (1977) Nature 266:550-52; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminoptenin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind ePSGL-1, e.g., using a standard ELISA assay.

Alternative to preparing monoclonal antibody-secreting hybridomas, a monoclonal anti-ePSGL-1 antibody can be identified and isolated by screening a recombinant combinatorial immunoglobulin library (e.g., an antibody phage display library) with ePSGL-1 respectively to thereby isolate immunoglobulin library members that bind ePSGL-1. Kits for generating and screening phage display libraries are commercially available (e.g., the Pharmacia Recombinant Phage Antibody System, Catalog No. 27-9400-01; and the Stratagene SurfZAP.™. Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734; Hawkins et al. (1992) J. Mol. Biol. 226:889-896; Clarkson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nuc. Acid Res. 19:4133-4137; Barbas et al. (1991) Proc. Natl. Acad. Sci. USA 88:7978-7982; and McCafferty et al. (1990) Nature 348:552-554.

Antibodies according to the invention can be used to detect ePSGL-1 protein (e.g., in a cellular lysate or cell supernatant) in order to evaluate the abundance and pattern of expression of the protein. Such antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotniazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

B. Isolated Nucleic Acid Molecules According to the Invention

The cDNA for ePSGL-1 and the amino acid sequence encoded thereby are shown in SEQ ID NOs: 1 and 2, respectively. The present invention encompasses isolated nucleic acid molecules that encode ePSGL-1 proteins or biologically active portions thereof, as well as nucleic acid fragments sufficient for use as hybridization probes to identify ePSGL-1-encoding nucleic acid molecules (e.g., ePSGL-1 mRNA) and fragments for use as PCR primers for the amplification or mutation of ePSGL-1 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., a nucleic acid molecule having the nucleotide sequence of SEQ ID NO: 1, or a portion thereof, can be isolated using standard molecular biology techniques and the sequence information provided herein. Using all or portion of the nucleic acid sequence of SEQ ID NO: 1 as a hybridization probe, ePSGL-1 nucleic acid molecules can be isolated using standard hybridization and cloning techniques (e.g., as described in Sambrook, J., Fritsh, E. F., and Maniatis, T. Molecular Cloning: A Laboratory Manual, 2.sup.nd. ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO: 1 can be isolated by the polymerase chain reaction (PCR) using synthetic oligonucleotide primers based upon the sequence of SEQ ID NO: 1. A nucleic acid according to the invention can be amplified using cDNA, mRNA or, alternatively, genomic DNA as a template and appropriate oligonucleotide primers according to standard PCR amplification techniques. Furthermore, oligonucleotides corresponding to ePSGL-1 nucleotide sequences can be prepared by standard synthetic techniques, e.g., using an automated DNA synthesizer.

In a preferred embodiment, the isolated nucleic acid molecules of the invention comprise the nucleotide sequence shown in SEQ ID NO: 1, a complement of the nucleotide sequence shown in SEQ ID NO: 1, or a portion of any of these nucleotide sequences. A nucleic acid molecule which is complementary to the nucleotide sequence shown in SEQ ID NO: 1, is one which is sufficiently complementary to the nucleotide sequence shown in SEQ ID NO: 1 such that it can hybridize to the nucleotide sequence shown in SEQ ID NO: 1 thereby forming a stable duplex.

In still another preferred embodiment, an isolated nucleic acid molecule of the present invention comprises a nucleotide sequence which is at least about 80%, 85%, 90%, 91%, 92%, 93%, 94%, 95%, 96%, 97%, 98%, 99% or more identical to the entire length of the nucleotide sequence shown in SEQ ID NO: 1. In another embodiment, an isolated nucleic acid molecule of the present invention comprises a nucleotide sequence which is at least about 80%, 85%, 90%, 91%, 92%, 93%, 94%, 95%, 96%, 97%, 98%, 99% or more identical to the mature extracellular domain of an ePSGL-1 molecule, namely, from nucleotide position 55 to nucleotide position 1317 of SEQ ID NO: 1. Moreover, the nucleic acid molecules used in the methods of the invention can comprise only a portion of the nucleic acid sequence of SEQ ID NO: 1, for example, a fragment which can be used as a probe or primer or a fragment encoding a portion of a ePSGL-1 protein, e.g., a biologically active portion of an ePSGL-1 protein. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO: 1 of an anti-sense sequence of SEQ ID NO: 1 or of a naturally occurring allelic variant or mutant of SEQ ID NO: 1. In one embodiment, a nucleic acid molecule used in the methods of the present invention comprises a nucleotide sequence which is greater than 100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, or more nucleotides in length and hybridizes under stringent hybridization conditions to a nucleic acid molecule of SEQ ID NO: 1.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.1 5M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# of A+T bases)+4(\# of G+C bases)$. For hybrids between 18 and 49 base pairs in length, $T_m(° C.)=81.5+16.6(\log_{10}[Na+])+0.41(\% G+C)-(600/N)$, where N is the number of bases in the hybrid, and [Na+] is the concentration of sodium ions in the hybridization buffer ([Na+] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C., see e.g., Church and Gilbert (1984) Proc. Natl. Acad. Sci. USA 81:1991-1995, (or alternatively 0.2×SSC, 1% SDS).

Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an ePSGL-1 protein, such as by measuring a level of a ePSGL-1 encoding nucleic acid in a sample of cells from a subject, e.g., detecting ePSGL-1 mRNA levels or determining whether a genomic ePSGL-1 gene has been mutated or deleted.

The present invention further includes nucleic acid molecules comprising the nucleotide sequence of SEQ ID NO:1 or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of ePSGL-1 (e.g., the sequence of SEQ ID NO:2) without altering the biological activity, whereas an "essential" amino acid residue is required for biological activity. For example, amino acid residues comprising fragments which are capable of interacting with equine P-selectin or which are capable of inhibiting equine P-selectin-mediated cellular adhesion or cellular migration are not likely to be amenable to alteration.

Mutations can be introduced into SEQ ID NO: 1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Polypeptides including one or more such conservative substitutions are termed "conservative variations" or "conservative variants" of a respective parent polypeptide. Further, the biological function between parent and conservative variant are substantially conserved. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an ePSGL-1 protein is preferably replaced with another amino acid residue from the same side chain family. Alternatively, in another embodiment, mutations can be introduced randomly along all or part of an ePSGL-1 coding sequence, such as by saturation mutagenesis, and the resultant mutants can be screened for ePSGL-1 biological activity to identify mutants that retain activity. Following mutagenesis of SEQ ID NO: 1 the encoded protein can be expressed recombinantly and the activity of the protein can be determined using the assay described herein.

Given the coding strand sequences encoding ePSGL disclosed herein, antisense nucleic acids of the invention can be designed according to the rules of Watson and Crick base pairing. The antisense nucleic acid molecule can be complementary to the entire coding region of ePSGL-1 mRNA, but more preferably is an oligonucleotide which is antisense to only a portion of the coding or noncoding region of ePSGL-1 mRNA. For example, the antisense oligonucleotide can be complementary to the region surrounding the translation start site of ePSGL-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomet- hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten- yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the ePSGL-1 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4(1):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. (1996) Proc. Natl. Acad. Sci. 93:14670-675.

PNAs of ePSGL-1 nucleic acid molecules can be used in the therapeutic and diagnostic applications described herein. For example, PNAs can be used as antisense or antigene agents for sequence-specific modulation of gene expression by, for example, inducing transcription or translation arrest or inhibiting replication. PNAs of ePSGL-1 nucleic acid molecules can also be used in the analysis of single base pair mutations in a gene, (e.g., by PNA-directed PCR clamping); as "artificial restriction enzymes" when used in combination with other enzymes, e.g., S1 nucleases (Hyrup B. et al. (1996) supra; or as probes or primers for DNA sequencing or hybridization (Hyrup B. et al. (1996) supra; Perry-O'Keefe et al. (1996) supra).

In another embodiment, PNAs of ePSGL-1 can be modified, e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of ePSGL-1 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. et al. (1996) supra). The synthesis of PNA-DNA chimeras can be performed as described in Hyrup B. et al. (1996) supra and Finn P. J. et al. (1996) Nucleic Acids Res. 24(17):3357-63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) Nucleic Acid Res. 17:5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) Bioorganie Med. Chem. Lett. 5:1119-11124).

In other embodiments, the oligonucleotides used in the methods of the invention may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958-976) or intercalating agents. (see, e.g., Zon (1988) Pharm. Res. 5:539-549). To this end, the oligonucleotide may be conjugated to another molecule (e.g., a peptide, hybridization triggered cross-linking agent, transport agent, or hybridization-triggered cleavage agent).

A DNA encoding other fragments and altered forms of ePSGL-1 of the invention may be prepared by expression of modified DNAs in which portions of the full-length sequence have been deleted or altered. Substantial deletions of the ePSGL-1 sequence can be made while retaining the protein's activity. For example, ePSGL-1s comprising the sequence from amino acid 1 to amino acid 286 of SEQ ID NO:2 retain the equine P-selectin protein binding activity. Construction of DNAs encoding these and other active fragments or altered forms of ePSGL-1 may be accomplished in accordance with methods known to those skilled in the art.

The isolated DNA used in the methods of the invention may be operably linked to an expression control sequence such as the pMT2 or pED expression vectors disclosed in Kaufinan et al., Nucleic Acids Res. 19, 4485-4490 (1991), in order to produce the ePSGL-1 recombinantly. Many suitable expression control sequences are known in the art. General methods of expressing recombinant proteins are also known and are exemplified in R. Kaufman, Methods in Enzymology 185, 537-566 (1990). As defined herein "operably linked" means enzymatically or chemically ligated to form a covalent bond between the isolated DNA of the invention and the expression control sequence, in such a way that the ePSGL-1 is expressed by a host cell which has been transformed (transfected) with the ligated DNA/expression control sequence.

C. Recombinant Expression Vectors and Host Cells According to the Invention

The invention (e.g., the screening assays described herein) includes the use of vectors, preferably expression vectors, containing a nucleic acid encoding an ePSGL-1 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors according to the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., ePSGL-1 proteins, mutant forms of ePSGL-1 proteins, fusion proteins, and the like).

The recombinant expression vectors according to the invention can be designed for expression of ePSGL-1 molecules in prokaryotic or eukaryotic cells. For example, ePSGL-1 proteins can be expressed in bacterial cells such as E. coli, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or nonfusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in ePSGL-1 activity assays, (e.g., direct assays or competitive assays described in detail below), or to generate antibodies specific for ePSGL-1 proteins.

In another embodiment, a nucleic acid of the invention is expressed in mammalian cells using a mammalian expression vector. Examples of mammalian expression vectors include pCDM8 (Seed, B. (1987) Nature 329:840) and pMT2PC (Kauftnan et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells, see chapters 16 and 17 of Sambrook, J. et al., Molecular Cloning: A Laboratory Manual, 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid).

The invention also includes a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to ePSGL-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, Trends in Genetics, 1:1 (1986).

As well, the invention further includes a recombinant vector capable of providing ribonucleic acid into a cell sufficient to inhibit genetic expression by RNA interference (RNAi). RNAi is now understood to be a common biological mechanism which, by knowledgeable manipulation, can be taken advantage of to silence target genes. Ribonucleic acids useful in RNAi form a double-stranded molecule with a first strand consisting of an RNA sequence which corresponds to a nucleotide sequence of the pre-selected target gene and a second strand consisting of RNA which is complementary to the nucleotide sequence of the target gene. Genetic inhibition by RNAi is well known to the artisans and is disclosed in, for example, U.S. Pat. No. 6,506,559 to Fire et al.

Another aspect of the invention pertains to the use of host cells into which a ePSGL-1 nucleic acid molecule of the invention is introduced, e.g., an ePSGL-1 nucleic acid molecule within a recombinant expression vector or an ePSGL-1 nucleic acid molecule containing sequences which allow it to homologously recombine into a specific, site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an ePSGL-1 protein can be expressed in bacterial cells such as E. coli, insect cells, yeast or mammalian cells (such as Chinese hamster ovary cells (CHO) or monkey kidney fibroblast (COS) cells). Other suitable host cells are known to those skilled in the art. A number of types of cells may act as suitable host cells for expression of the ePSGL-1 protein. Suitable host cells are capable of attaching carbohydrate side chains characteristic of functional ePSGL-1 protein. In addition, suitable host cells are capable of providing appropriate sulfation characteristic of funational ePSGL-1 protein. Such capabilities may arise by virtue of the presence of a suitable glycosylating and/or sulfating enzyme within the host cell, whether naturally occurring, induced by chemical mutagenesis, or through transfection of the host cell with a suitable expression plasmid containing a DNA sequence encoding the glycosylating and/or sulfating enzyme. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, or HaK cells. A particularly preferred host cell line is the CHO (C2GnT+Fuc-TVII) cell line utilized in Example 3.

The ePSGL-1 protein may also be produced by operably linking the isolated DNA of the invention and one or more DNAs encoding suitable post-translational modifying enzymes to suitable control sequences in one or more insect expression vectors, and employing an insect expression system. Materials and methods for baculovirus/insect cell expression systems are commercially available in a kit form from, e.g., Invitrogen, San Diego, Calif., U.S.A. (the MAX-BAC (registered trademark) kit), and such methods are well known in the art, as described in Summers and Smith, Texas Agricultural Experiment Station Bulletin No. 1555 (1987), incorporated herein by reference. Soluble forms of the ePSGL-1 protein may also be produced in insect cells using appropriate isolated DNAs as described above.

Alternatively, it may be possible to produce the ePSGL-1 protein in lower eukaryotes such as yeast or in prokaryotes such as bacteria. Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the P-selectin ligand-1 protein is made in yeast or bacteria, it is necessary to attach the appropriate carbohydrates and sulfates to appropriate sites on the protein moiety covalently, in order to obtain the modified P-selectin ligand-1 protein. Such covalent attachments may be accomplished using known chemical or enzymatic methods.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. Molecular Cloning: A Laboratory Manual, 2nd ed., Cold Spring Harbor Laboratory, Cold Spring Harbor Laboratory Press, Cold Spring Harbor, N.Y., 1989, and other laboratory manuals.

A host cell used in the methods of the invention, such as a prokaryotic or eukaryotic host cell in culture, can be used to produce (i.e., express) an ePSGL-1 protein. Accordingly, the invention further provides methods for producing an ePSGL-1 protein using the host cells of the invention. In one embodiment, the method comprises culturing the host cell of the invention (into which a recombinant expression vector encoding an ePSGL-1 protein has been introduced) in a suitable medium such that an ePSGL-1 protein is produced. In another embodiment, the method further comprises isolating an ePSGL-1 protein from the medium or the host cell.

D. Methods of Use According to the Invention

The present invention provides for both prophylactic and therapeutic methods of treating, preventing, or reducing tissue or organ damage in an equine subject, at risk of acute inflammatory response related to, e.g., intestinal ischemia, colitis and neonatal septicemia. With regard to both prophylactic and therapeutic methods of treatment, such treatments may be specifically tailored or modified, based on knowledge obtained from the field of pharmacogenomics. "Treatment," as used herein, is defined as the application or administration of a therapeutic agent to an equine subject, or application or administration of a therapeutic agent to an isolated tissue or cell line from an equine subject, who has a disease or disorder, a symptom of disease or disorder or a predisposition toward a disease or disorder, with the purpose of curing, healing, alleviating, relieving, altering, remedying, ameliorating, improving or affecting the disease or disorder, the symptoms of disease or disorder or the predisposition toward a disease or disorder.

"Pharmacogenomics," as used herein, refers to the application of genomics technologies such as gene sequencing, statistical genetics, and gene expression analysis to drugs in clinical development and on the market. More specifically, the term refers to the study of how a subject's genes determines the subject's response to a drug (e.g., a patient's "drug response phenotype", or "drug response genotype").

Thus, another aspect of the invention provides methods for tailoring an equine subject's prophylactic or therapeutic treatment with either the P-selectin antagonists of the present invention or P-selectin ligand-1 modulators according to that individual's drug response genotype. Pharmacogenomics allows a veterinarian or physician to target prophylactic or therapeutic treatments to subjects who will most benefit from the treatment and to avoid treatment of subjects who will experience toxic drug-related side effects.

(i) Prophylactic and Therapeutic Methods According to the Invention

In general, it is known that P-selectin has several functions related to vascular injury and thrombosis including mediating rolling of leukocytes on vascular endothelium, promoting interaction of platelets with leukocytes resulting in leukocyte activation and release of tissue factor rich microparticles from these activated cells and or pro-inflammatory mediators the further activate endothelium cells to promote more leukocyte capture; capture of leukocyte derived microparticles on clots and endothelium to promote clot growth; and plugging of microvessels to extend areas of ischemia. Specific inhibitors of P-selectin interaction with its ligand PSGL would be expected to significantly reduce these events. In the case of equine rPSGL-Ig, this soluble ligand construct would be expected to bind to expressed equine P-selectin on endothelium and platelets and thus reduce the ability of native ePSGL-1 on the surface of leukocytes or leukocyte derived microparticles to bind. The effect of the presence of equine rPSGL-Ig would be to reduce inflammatory and thrombotic responses in situations resulting in increased equine P-selectin/ePSGL-1 interactions.

Inhibition of equine P-selectin/ePSGL-1 interactions may be particularly useful in thrombotic stroke. Reduction in formation of activated platelet/leukocyte complexes with rPGSL-Ig could improve microvascular flow downstream of the vascular obstruction by reducing vascular plugs due to platelet/leukocyte complexes formed as a result of P-selectin/ePSGL-1 interactions. This improved microvascular flow could reduce infarct growth and thus reduce the extent of long term damage to a tissue or organ. In addition, by reducing leukocyte/endothelial cell rolling, rPSGL-Ig could reduce the extent of reperfusion injury following clot lysis.

Use of rPSGL-Ig may also be beneficial in treating equine subjects with or susceptible to septicemic disorders. Septicemia is known to cause the release of inflammatory mediators from the activated blood cells. These agents are known to promote expression of P-selectin on platelets and endothelium cells. Reduction of these secondary inflammatory responses by early intervention with a selectin antagonist could prove to be very beneficial in reducing morbidity and mortality associated with septicemic conditions.

In one aspect, the invention provides a method for modulating, e.g., treating, preventing, or reducing organ or tissue damage, e.g., intestinal damage, caused by reperfusion injury following ischemia in an equine subject by administering to the subject a composition which includes an agent which modulates ePSGL-1 expression or ePSGL-1 activity, e.g., modulates equine P-selectin binding, modulates cellular adhesion, e.g., cell-to-cell adhesion (e.g., leukocyte-endothelial cell adhesion or leukocyte-platelet adhesion), and cell (e.g., leukocyte) adhesion to blood vessels, and modulates leukocyte rolling. Equine subjects at risk for ischemia and/or reperfusion injury can be identified by, for example, any or a combination of veterinarian diagnostic or prognostic assays known by one of skill in the art. Administration of a prophylactic or therapeutic agent, e.g., an ePSGL-1 molecule, or a fragment thereof having equine P-selectin ligand-1 activity, e.g., soluble ePSGL-1, or a soluble recombinant ePSGL-1 fusion protein, e.g., rPSGL-Ig, can occur prior to reperfusion, such that damage to tissue and organs is inhibited or reduced.

Methods of administering to an equine subject a P-selectin antagonist, e.g., an anti-P-selectin ligand-1 antibody, soluble P-selectin ligand-1, soluble ePSGL-1, or fragments thereof, or soluble rPSGL-Ig, to treating, preventing, or reducing organ or tissue damage following ischemia and/or reperfusion, include, but are not limited to, the following methods.

The soluble P-selectin antagonists of the invention are administered to a subject in the form of a pharmaceutical composition suitable for such administration. Such compositions typically include an effective amount of the active agent (e.g., protein or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELT (trademark) (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates ePSGL-1 activity (e.g., a fragment of a soluble ePSGL-1 molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystal line cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate ePSGL-1 activity can also be prepared in the form of suppositories (e.g., with conventional suppository bases such as cocoa butter and other glycerides) or retention enemas for rectal delivery.

In one embodiment, the agents that modulate ePSGL-1 activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates ePSGL-1 activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such ePSGL-1 modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the seventy of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an equine (e.g., a horse) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a therapeutic agent or a radioactive metal ion. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, Pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev:, 62:119-58 (1982). Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

(ii) Screening Assays

The invention further provides methods (also referred to herein as "screening assays") for identifying modulators, i.e., candidate or test compounds or agents (e.g., peptides, peptidomimetics, small molecules, ribozymes, or ePSGL-1 antisense molecules) which bind to ePSGL-1 proteins, have a stimulatory or inhibitory effect on ePSGL-1 expression or ePSGL-1 activity, or have a stimulatory or inhibitory effect on the expression or activity of an ePSGL-1 target molecule, e.g. P-selectin, or have an effect, e.g., inhibition of cellular migration or adhesion, on cells expressing an ePSGL-1 target molecule, e.g., endothelial cells and activated platelets. Compounds identified using the assays described herein may be useful in, for example, treating, preventing, or reducing tissue and organ damage due to acute inflammatory response.

Candidate/test compounds include, for example, 1) peptides such as soluble peptides, including Ig-tailed fusion peptides and members of random peptide libraries (see, e.g., Lam, K. S. et al. (1991) Nature 354:82-84; Houghten, R. et al. (1991) Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) Cell 72:767-778); 3) antibodies (e.g., polyclonal, monoclonal, humanized, anti-idiotypic, chimeric, and single chain antibodies as well as Fab, F(ab')$_2$ Fab expression library fragments, and epitope-binding fragments of antibodies); and 4) small organic and inorganic molecules (e.g., molecules obtained from combinatorial and natural product libraries).

The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example, in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed, Engl. 33:2061; and Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra).

Assays that may be used to identify compounds that modulate ePSGL-1 activity include assays for cell adhesion using $^{51}$Cr-labelled cells, e.g., leukocytes (as described in, for example, Kennedy et al. (2000) Br J Pharmacology 130(1): 95), and assays for cell migration, e.g., platelet, neutrophil and leukocyte migration (as described in, for example Kogaki et al. (1999) Cardiovascular Res 43(4):968) and Bengtsson et al. (1999) Scand J Clin Lab Invest 59(6):439).

In one aspect, an assay is a cell-based assay, in which a cell which expresses an ePSGL-1 protein or biologically active portion of the same that is believed to be involved in the binding of equine P-selectin (e.g., amino acid residues 19-328 of SEQ ID NO:2), is contacted with a test compound, and the ability of the test compound to modulate ePSGL-1 activity is determined. In a preferred embodiment, the biologically active portion of the ePSGL-1 protein includes a domain or motif that is capable of interacting with equine P-selectin or inhibiting equine P-selectin mediated cellular adhesion. Determining the ability of the test compound to modulate ePSGL-1 activity can be accomplished by monitoring, for example, cell adhesion or cell migration. The cell, for example, can be of mammalian origin, e.g., an endothelial cell or a leukocyte, preferably derived from an equine.

The ability of the test compound to modulate ePSGL-1 binding to a substrate or to bind to ePSGL-1 can also be determined. Determining the ability of the test compound to modulate ePSGL-1 binding to a substrate can be accomplished, for example, by coupling the ePSGL-1 substrate with a radioisotope or enzymatic label such that binding of the ePSGL-1 substrate to ePSGL-1 can be determined by detecting the labeled ePSGL-1 substrate in a complex. Alternatively, ePSGL-1 could be coupled with a radioisotope or enzymatic label to monitor the ability of a test compound to modulate ePSGL-1 binding to an ePSGL-1 substrate in a complex. Determining the ability of the test compound to bind ePSGL-1 can be accomplished, for example, by coupling the compound with a radioisotope or enzymatic label such that binding of the compound to ePSGL-1 can be determined by detecting the labeled ePSGL-1 compound in a complex. For example, ePSGL-1 substrates can be labeled with $^{125}I$, $^{35}S$, $^{14}C$, or $^{3}H$, directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to interact with ePSGL-1 without the labeling of any of the interactants. For example, a microphysiometer can be used to detect the interaction of a compound with ePSGL-1 without the labeling of either the compound or the ePSGL-1 (McConnell, H. M. et al. (1992) Science 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and ePSGL-1.

In yet another embodiment, an assay of the present invention is a cell-free assay in which an ePSGL-1 protein or biologically active portion thereof (e.g., a fragment of a ePSGL-1 protein which is capable of binding P-selectin) is contacted with a test compound and the ability of the test compound to bind to or to modulate (e.g., stimulate or inhibit) the activity of the ePSGL-1 protein or biologically active portion thereof is determined. Preferred biologically active portions of the ePSGL-1 proteins to be used in assays of the present invention include fragments which participate in interactions with non-ePSGL-1 molecules, e.g., fragments with high surface probability scores. Binding of the test compound to the ePSGL-1 protein can be, determined either directly or indirectly as described above. Determining the ability of the ePSGL-1 protein to bind to a test compound can also be accomplished using a technology such as real-time Biomolecular Interaction Analysis (BIA) (Sjolander, S. and Urbaniczky, C. (1991) Anal. Chem. 63:2338-2345; Szabo et al. (1995) Curr. Opin. Struct. Biol. 5:699-705). As used herein. "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In more than one embodiment of the above assay methods of the present invention, it may be desirable to immobilize either ePSGL-1 or equine P-selectin to facilitate separation of complexed from uncomplexed forms of one or both of the proteins, as well as to accommodate automation of the assay. Binding of a test compound to an ePSGL-1 protein, or interaction of an ePSGL-1 protein with equine P-selectin in the presence and absence of a test compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/-ePSGL-1 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or ePSGL-1 protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of ePSGL-1 binding or activity determined using standard techniques.

Other techniques for immobilizing proteins on matrices can also be used in the screening assays of the invention. For example, either an ePSGL-1 protein or an equine P-selectin molecule can be immobilized utilizing conjugation of biotin and streptavidin. Biotinylated ePSGL-1 protein or equine P-selectin protein can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with ePSGL-1 protein or equine P-selectin but which do not interfere with binding of the ePSGL-1 protein to its target molecule can be derivatized to the wells of the plate, and unbound target or ePSGL-1 protein is trapped in the wells by antibody conjugation. Methods for detecting such complexes, in addition to those described above for the GST-immobilized complexes, include immunodetection of complexes using antibodies reactive with the ePSGL-1 protein or P-selectin, as well as enzyme-linked assays which rely on detecting an enzymatic activity associated with the ePSGL-1 protein or P-selectin.

In yet another aspect of the invention, the ePSGL-1 protein or fragments thereof (e.g., a fragment capable of binding P-selectin) can be used as "bait proteins" in a two-hybrid assay or three-hybrid assay (see, e.g., U.S. Pat. No. 5,283, 317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, which bind to or interact with ePSGL-1 ("ePSGL-1-binding proteins" or "ePSGL-1-bp") and are involved in ePSGL-1 activity. Such ePSGL-1-binding proteins are also likely to be involved in the propagation of signals by the ePSGL-1 proteins or ePSGL-1 targets as, for example, downstream elements of an ePSGL-1-mediated signaling pathway. Alternatively, such ePSGL-1-binding proteins are likely to be ePSGL-1 inhibitors.

The two-hybrid system is based on the modular nature of most transcription factors, which consist of separable DNA-binding and activation domains. Briefly, the assay utilizes two different DNA constructs. In one construct, the gene that codes for a ePSGL-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an ePSGL-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the ePSGL-1 protein.

In another aspect, the invention pertains to a combination of two or more of the assays described herein. For example, a modulating agent can be identified using a cell-based or a cell-free assay, and the ability of the agent to modulate the activity of an ePSGL-1 antagonist can be confirmed in vivo, e.g., in an animal model, such as an animal model for ischemia. Animal models for ischemia and reperfusion include those described herein and those described in, at least, for example, Sarabi, et al. (2001) Exp. Neurol. 170(2):283-9; Descheerder, et al. (2001) J. Am. Soc. Echocardiogr 14(7): 691-7; Ohara, et al. (2001) Gene Trer. 8(11):837; and Dammers, et al. (2001) Br. J. Surg. 88(6):816-24.

Moreover, an ePSGL-1 modulator identified as described herein (e.g., an antisense ePSGL-1 nucleic acid molecule, an ePSGL-1-specific antibody, or a small molecule) can be used in an animal model to determine the efficacy, toxicity, or side effects of treatment with such a modulator. Alternatively, an ePSGL-1 modulator identified as described herein can be used in an animal model to determine the mechanism of action of such a modulator.

The contents of all references, patents and published patent applications specifically cited throughout this application, as well as the Figures and the Sequence Listing, are incorporated herein by reference. The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. EXAMPLES

Example 1

Characterization of ePSGL-1 cDNA and Polypeptide

Peripheral Blood Mononuclear Cell (PBMC) collection. Blood from a normal healthy horse was collected into 3.8% sodium citrate. Gravity separation by rouleaux formation of the Red Blood Cells from the White Blood Cells was accomplished by allowing the equine whole blood to settle undisturbed at 20° C. temperature for 45 minutes. The Platelet Leukocyte Rich Plasma (PLRP) was collected in a sterile tube, which was then filled with Phosphate Buffered Saline (PBS) and spun at 300×g for 10 min. The supernatant was discarded and the pellet resuspended with 15 mL of PBS. In order for the cells to segregate into three layers, 10 mL of Histopaque-1077 (Sigma®) was added and centrifuged at 600×g for 20 min. The PBMC rich interphase was collected and washed twice with PBS. Cells were then cultured overnight in medium (RPMI-1640 supplemented with 10% Newborn Calf Serum and 1% Penicillin/Streptomycin), at 37° C. All experiments conformed to the guidelines of the care and use of research animals and human subjects of the National Institutes of Health and were approved by the Institutional Animal Care and Use Committee of the University of Wisconsin, Madison.

Total RNA isolation. PBMCs were lysed with TRI Reagent® (SIGMA) and total RNA isolated following the manufacturer's protocol. Total RNA integrity was confirmed by demonstrating the twice intensity of 28 s band than 18 s band on a 1.0% agarose gel.

Reverse Transcription. cDNA synthesis was done with the AMV reverse transcriptase enzyme (Invitrogen) according to the manufacturer's protocol using either random hexamer or oligo dT primers at an annealing temperature of 42° C. Successful cDNA synthesis was verified by performing a PCR amplification of the beta-actin gene.

Sequencing of the equine PSGL-1 gene. PCR amplification was done initially using degenerate primers derived from the conserved homologous region between mouse and human PSGL-1 (hPSGL-1) published sequences (GI: 31982018 and GI: 6031197). Upon generating an equine PSGL-1 (ePSGL-1) fragment, subsequent sequences were generated from equine gene-specific primers for 3' and 5' RACE PCR. GeneRacer™ kit (Invitrogen Corporation, Carlsbad, Calif.) and SMART™ (Spliceosome-Mediated RNA Trans-Splicing) (BD, Franklin Lakes, N.J.) kit were used separately to amplify the 3' and 5' un-translated region of equine PSGL-1 cDNA according to the manufacturers' instructions. All primers are listed in table 1. The PCR products were run on a 1.2% agarose gel and then purified from the gel with the Qiagen gel purification kit (Qiagen, Valencia, Calif.), and sequenced. All sequences obtained were performed searching with the publicly available search algorithm BLAST algorithm against the human PSGL-1 using the National Center for Biotechnology Information (NCBI).

TABLE 1

List of primers used to sequence equine PSGL-1 cDNA.

| Primers | Sequences (5' to 3') | Location (bp) |
|---|---|---|
| Forward | GCTGTCAACGATACGCTACGTAACG (SEQ. ID NO: 24) | 3' GeneRacer kit |
| Nested Forward | CGCTACGTAACGGCATGACAGTG (SEQ. ID NO: 25) | 3' GeneRacer kit |
| Forward 3 | CATCTCATCCCTGTTGCCTGAT (SEQ. ID NO: 26) | Human 1062-1084 |

TABLE 1-continued

List of primers used to sequence equine PSGL-1 cDNA.

| Primers | Sequences (5' to 3') | Location (bp) |
|---|---|---|
| Forward 2 | CACAGACCACTCCACTGGCAGCCATGGAGG (SEQ. ID NO: 27) | Human 721-750 |
| Forward 1 | ATGCCTCTGCAACTCCTCCT (SEQ. ID NO: 28) | Human 1-20 |
| Forward 4 | AGGCCCAGTCCACAGTTCTAGC (SEQ. ID NO: 29) | Equine 743-764 |
| Reverse 2 | CCAACAGGGCCAGGATAAGG (SEQ. ID NO: 30) | Equine 876-895 |
| Reverse 1 | ACCTGTGGAATTGAGCCTGAAT (SEQ. ID NO: 31) | Equine 1218-1239 |
| Forward Long | CTAATACGACTCACTATAGGGCA AGCAGTGGTATCAACGCAGAGT (SEQ. ID NO: 32) | 5'SMART Racer kit |
| Forward Short | CTAATACGACTCACTATAGGGC (SEQ. ID NO: 33) | |
| Reverse | CGTAGCTGCGGGTTGGGTGGTCA (SEQ. ID NO: 34) | Equine 719-743 |
| Nested Reverse | TCCAGGAAGGGAGGGTTTGTA (SEQ. ID NO: 35) | Equine 374-395 |

Equine PSGL-1 cDNA contains 2065 nucleotides (nt) including a 5' untranslated region of 54 nt, a single open reading frame (ORF) of 1263 nt and a 3' untranslated region of 748 nt (FIG. 1; SEQ ID NO:1). The ORF encodes 420 amino acids consisting of a 328-residue extracellular domain, a 23-residue transmembrane domain and a 69 residue cytoplasmic tail (SEQ ID NO:2). Comparatively, hPSGL-1 is a dimeric mucin-like 120-kDa glycoprotein whose cDNA contains 2041 nt. The ORF encodes a 392-412 residue type 1 polypeptide depending on whether the extracellular region contains 14 or 16 decameric repeats. The N-terminus of the human protein contains a signal sequence with the putative cleavage site between luecine and glutamine at residues 18-19. A propeptide spanning residues 19-41 is removed in leukocytes by paired basic amino acid converting enzymes (PACE) at the tetra-peptide consensus residues 38-41 (R-N-R-R) (Li et al. 1996). As a result, the mature hPSGL-1 protein which starts at residue 42, is comprised of a 258-278 residue extracellular domain, a 23-residue transmembrane domain and a 69 residue cytoplasmic tail. The first 18-amino acid sequence of ePSGL-1 reveals 78% homology to the hPSGL-1 signal peptide with the same peptide consensus residues 18-20 (Leu-Glu-Leu), suggesting a putative signal sequence cleavage site at 18-19. However, the absence of a PACE cleavage site suggests that ePSGL-1 may not process the propeptide (Rehemtulla and Kaufman 1992) (FIG. 2A). As such, the mature ePSGL-1 begins at residue 19, followed by an extracellular $NH_2$ terminal sequence, consensus repeats, a transmembrane region, and cytoplasmic domain, which follows the pattern of hPSGL-1.

Figure 10:
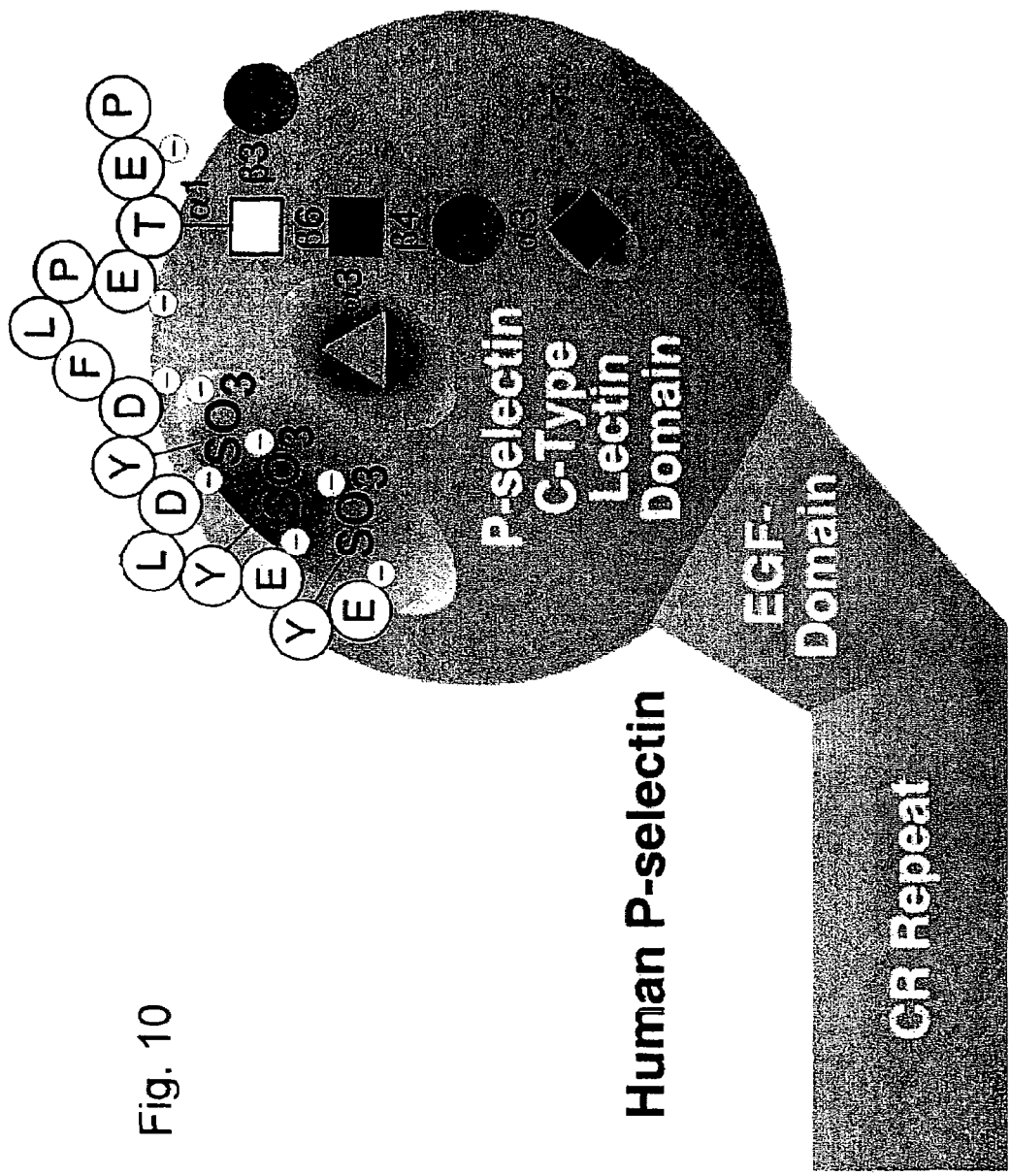
FIG. 10. Schematic representation of human PSGL-1 amino terminus (fifteen amino acid residues spanning positions 45-59) contacting human P-selectin (based on Leppanen et al. J. Biol. Chem. 275:39569 (2000)).
Figure 11:
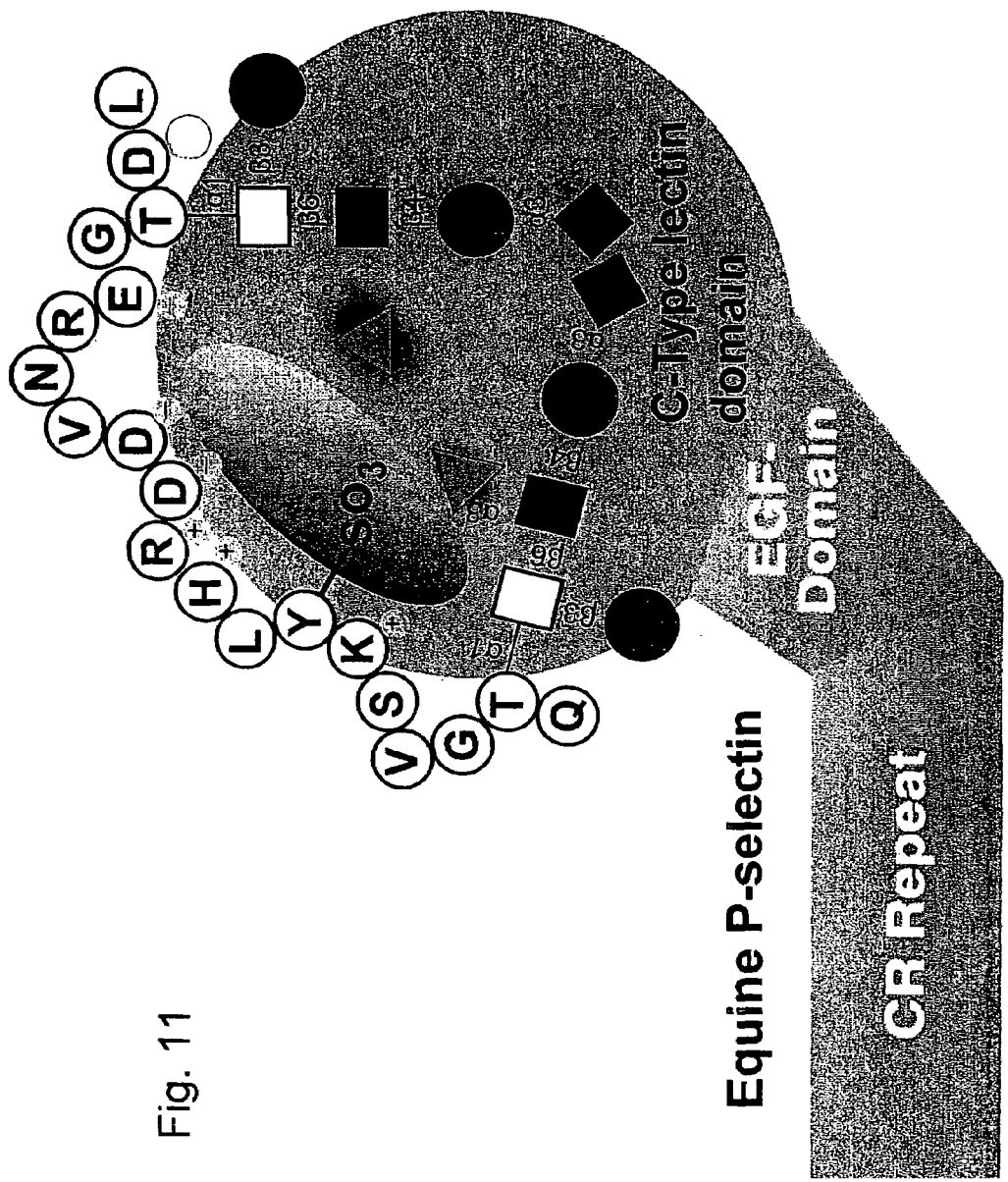
FIG. 11. Schematic representation of equine PSGL-1 amino terminus (twenty amino acids spanning positions 24-43) contacting equine P-selectin.

The potential P-selectin binding sites near the extreme N terminus of hPSGL-1 (residues 42-57) includes two threonine O-glycosylation sites (Thr44, Thr57) and three tyrosine sulfation sites (Tyr46, Tyr48, Tyr 51), which are located 6 to 11 residues from the Thr57 residue. Three consensus sites for N-glycosylation exist within the extracellular domain. A number of experimental results indicate that the O-glycans and tyrosine sulfation on PSGL-1 are responsible for high affinity binding interactions between PSGL-1 and P-selectin (Cummings 1999; Rodgers et al. 2001). More recent studies employing cocrystal structure analysis have determined that optimal binding requires a specific stereochemical configuration of the 3 tyrosine sulfate residues, Thr57 association with a core-2 based O-glycan expressing the sialyl Lewis x antigen and adjacent peptide determinants, but N-glycans may not be required (Leppanen et al. 2000; Somers et al. 2000). FIG. 10 illustrates binding of HPSGL-1 to human P-selectin according to the most recent studies.

ePSGL-1 contains only 1 potential site for tyrosine sulfation and 1 potential site for N-glycosylation in the extreme amino terminal domain (residues 19-41) and 82 Ser/Thr residues in the extracellular domain as potential sites for O-glycosylation. The only tyrosine (Tyr30), within the consensus Ser-Lys-Tyr-Leu sequence, is located within 11 residues of the threonine (Thr41) residue. Based on the predictions of Bundgaard et al. (1997), a neutral or acidic charge of the residue in the amino-terminal position (−1) of the tyrosine is critical for sulfation whereas a basic residue will abolish it. In addition, a basic residue in amino-terminal position −2 enhances sulfation (Bundgaard et al. 1997). For ePSGL-1, the presence of the basic residue (Lys29) at position −1 and absence of a basic residue (Ser28) at −2, suggests that sulfation at Tyr30 is unlikely. That several publications have demonstrated the importance of tyrosine sulfation for high affinity binding of both human and murine PSGL-1 to P-selectin creates the potential for a paradigm shift in the way that ePSGL-1 interacts with P-selectin. If Tyr30 is sulfated, then the charge at amino-terminal position at −1 and −2 (as proposed in the model of tyrosine sulfation by Bundgaard et al. 1997), may not apply to equine PSGL-1. Alternatively, tyrosine sulfation in the extreme amino terminal of ePSGL-1 may not be required for high affinity binding to P-selectin if other potential sites of sulfation are able to confer high affinity binding. FIG. 11 depicts a model of how ePSGL-1 may bind equine P-selectin based upon the presently-described study; however, no particular theory or mechanism of operation is adopted nor claimed herein.

The total number of Thr/Ser residues in the extracellular domain of ePSGL-1 is greater than hPSGL-1 (82 vs. 70-74, respectively), while the number of Thr residues for the 2 species is similar (57 vs. 56-60, respectively). Consequently, greater number of Ser residues in ePSGL-1 (24 vs. 14) may be a mechanism by which high affinity interaction between PSGL-1 and P-selectin is achieved in the equine.

The extreme N-termini of ePSGL-1 and hPSGL-1 do share some degree of homology for potential sites for O-glycosylation in the configuration of tyrosine to Ser/Thr residues. In ePSGL-1, Thr41 lies within 11 residues of Tyr30, which is the same number of amino acids that separate Tyr46 and Thr57 in hPSGL-1. In addition, ePSGL-1 has a greater number of Ser/Thr residues in the extracellular domain than hPSGL-1, which suggests that high affinity interaction with P-selectin may be achieved through highly clustered O-glycans or differentially glycosylated residues rather than tyrosine sulfation (Lasky 1995; Wilkins et al 1996). This premise is supported by the fact that murine PSGL-1 may rely more on O-glycosylation in the extracellular domain and other peptide components for high affinity binding to P-selectin than hPSGL-1 does (Li et al. 2003). Compared to the requirement of O-glycan in PSGL-1/P-selectin binding, enzymatic removal of N-linked glycans does not affect PSGL-1 binding to P-selectin. ePSGL-1 contains only one potential site for N-glyconsylation (Asn102-Leu103-Thr104), while hPSGL-1 has three (FIG. 1). In summary, these unique characteristics of equine PSGL-1 make it likely that it uses a different configuration of residues to bind to equine P-selectin. The lack of conservation of the P-selectin binding domain suggests some flexibility in the configuration of the actual P-selectin recognition site between species.

One notable feature in hPSGL-1 is the variable number (14 to 16) of tandem decameric repeats with the consensus sequence A-T/M-E-A-Q-T-T-X-P/L-A/T, where X can be either P, A, Q, E or R (Afshar-Kharghan et al. 2001; Sako et al. 1993). Similarly, ePSGL-1 protein also contains fourteen tandem decameric repeats with the consensus sequence S/T-T-Q/E-P-A-A-T-E-A/V-L spanning residues 151-290 (FIG. 1), which differs markedly from the hPSGL-1 consensus repeat. However, if the equine decameric repeats are shifted to start at residue 156 and end at position 285, it forms 13 decameric amino acid repeats with a consensus sequence A-T-E-A/V-L-T/S-T-Q/E-P-A which shows somewhat greater homology to hPSGL-1. Combining the horse decameric repeats to form 20 residues for each group, rather than 10 (FIG. 3, A), will display an even greater consensus between the repeating ePSGL-1 units (FIG. 3, B).

At the proposed junction of the extracellular and transmembrane domain of ePSGL-1, there is a single extracellular cysteine (Cys328) residue. The corresponding cysteine in human PSGL-1 (at position 320 for the 16 decapeptide repeat) is responsible for hPSGL-1 dimerization, which is more important for triggering cell signaling than mediating cell adhesion (Cummings 1999). However, whether this covalent dimerization is required for P-selectin recognition remains unresolved (Snapp et al. 1998; Epperson et al. 2000). Besides the covalent dimerization via Cys320, Epperson also found a transmembrane domain (TMD)-dependent non-covalent dimerization of human PSGL-1 via self-association (Epperson et al. 2000). Because the transmembrane and cytoplasmic domains of ePSGL-1 and hPSGL-1 share a high degree of homology, 91% and 74%, respectively (FIG. 2B, 2C), the TMD of equine PSGL-1 may also be involved in the non-covalent dimerization and mediating the cell signaling.

Taken together, there is an overall similarity of 71% between equine and human PSGL-1 ORF nucleotides. ePSGL-1 and hPSGL-1 contain a similar domain organization and high degree of homology in the carboxyl-terminal region. However, the absence of a propeptide, the single tyrosine in the extreme NH2-terminus region (which may not be sulfated), and the greater number of serine residues in the extracellular domain and 7 consensus repeats of 20 residues characterize the uniqueness of ePSGL-1 when compared to hPSGL-1. The nucleotide sequence data reported herein has been submitted to GenBank at accession number AY298766.

Example 2

Construction of an Equine PSGL-1 Plasmid: pPSGL1-Myc/His

In this example, cDNA coding the equine PSGL-1 (ePSGL-1) Open Reading Frame (ORF) was amplified by polymerase chain reaction (PCR) using primers that add the unique restriction sites Xho I and BamH I on the 5' and 3' ends, respectively. FIG. 4 illustrates the appropriate step-by-step methodology. The ePSGL-1 fragment was purified by agarose electrophroresis and subsequently cloned into a TOPO vector for sequencing. After confirmation of the nucleotide sequence, the ePSGL-1 fragment was excised with XhoI and BamHI and subcloned into the pcDNA3.1/Myc-His (−) expression vector to obtain a construct according to the invention.

Example 3

Establishment of Cell Lines Expressing Functional ePSGL-1 on their Cell Surface

A functional ePSGL-1 protein is expected to specifically-bind equine P-selectin and efficiently mediate cell signaling after its binding. It is recognized that post-translation modifications of human PSGL-1 is required for efficient binding to P-selectin. Accordingly, as shown schematically in FIG. 5, three types of CHO cells: Core2 (C2GnT=core 2 beta-1,6-N-acetylglucosaminyl transferase) expessing only; Fucosyl-transferase VII (Fuc-TVII) expressing only; and C2GnT+Fuc-TVII expressing are co-transfected with the plasmid pePSGL-1-Myc/His to express post-translational modified ePSGL-1 proteins on the cell surface. ePSGL-1 CHO cell binding to P-selectin platelets may then be assessed by flow cytometry to determine relative levels of PSGL-1/P-selectin binding.

Furthermore, if the recombinant ePSGL-1 expressed on CHO cells is functional, the binding with P-selectin peptide will mediate cell signaling, which is evaluated by immunoblot analysis and real-time PCR, as also shown in FIG. 5. In particular, immunoblot analysis may be performed to detect statistically-significant alterations in MCP-1, IL-8 and MAPK (ERK½), levels of which are known to be affected by PSGL-1 intracellular signaling (procedures described in, for example, Hidari KI, Weyrich AS, Zimmerman Ga., et al. (1997). J. Biol. Chem. 272: 28750-28756).

Example 4

Cloning and Expression of Chimeric ePSGL1-Ig Protein

Figure 6:
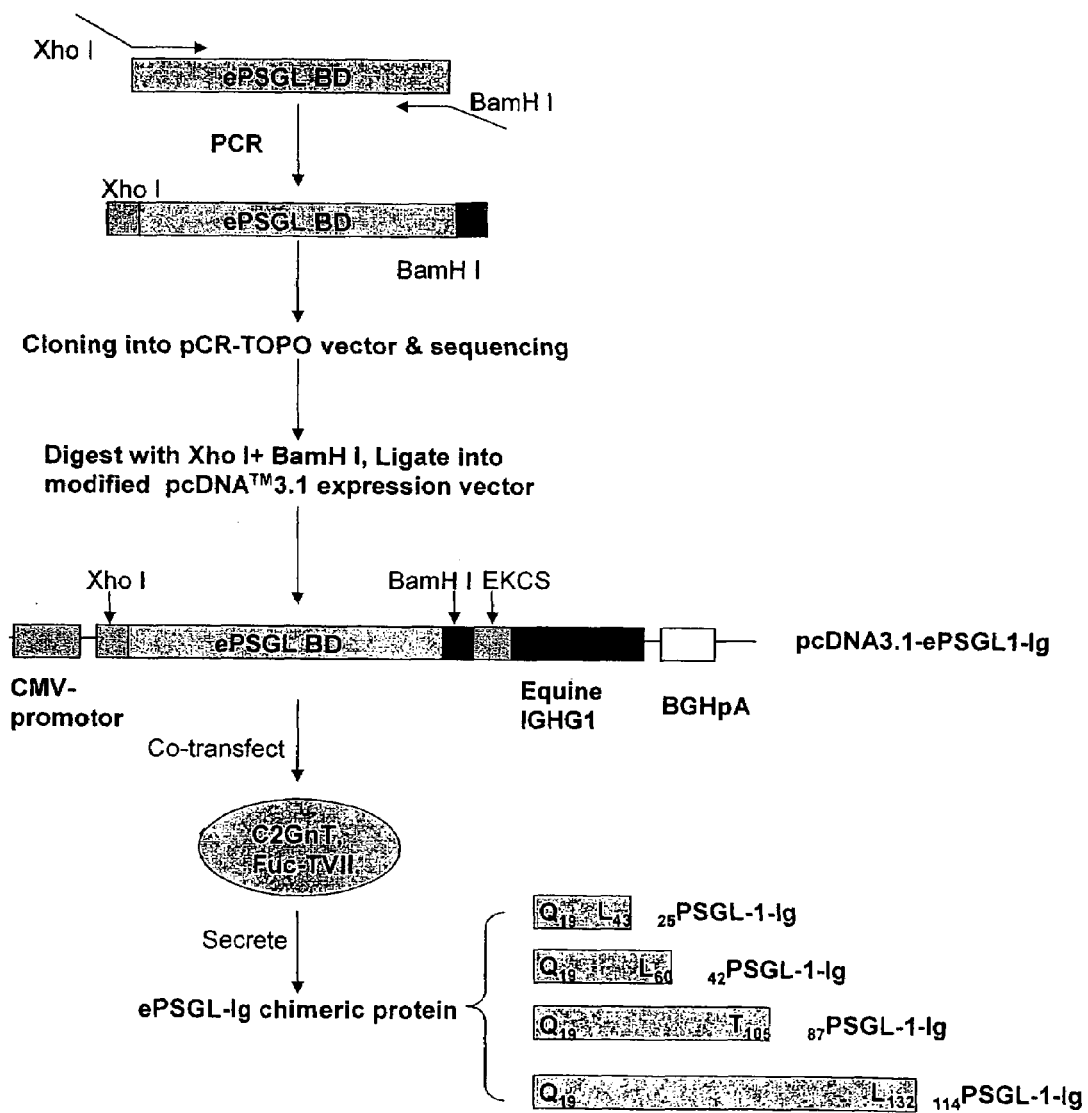
FIG. 6. Schematic illustration showing the steps of cloning and expressing representative ePSGL-1-Ig fusion proteins.

As illustrated in FIG. 6, fragments of extracellular domain from equine PSGL-1 are amplified by PCR using primers that add unique restriction sites Xho I and BamH I on the 5' and 3' ends, respectively. The resulting fragment is purified by agarose electrophroresis and cloned into a TOPO vector to be sequenced by standard methodology. After the fragments sequence is confirmed, the fragment is recovered by digestion with Xho I and BamH I, and subcloned into a modified pcDNA3.1 expression vector containing an enterokinase cleavage site (EKCS) and equine heavy chain IgG on the C-terminal of insertion. A suitable expression vector containing a cytomegalovirus (CMV) promoter and a bovine growth hormone polyadenylation signal (BGHpA) to enhance mRNA stability is described in Qiu et al. Journal of Virology 73:9145-9152 (1999).

The above-described methodology is applicable in the construction of various recombinant ePSGL-1-Ig chimeric proteins and it can be realized that selection of appropriate primers will determine the exact fragment of extracellular domain to be included in the construct. Based upon PSGL/P-selectin binding models (see, e.g., FIGS. 10 and 11 and discussion related thereto), chimeric constructs including the following ePSGL-1 amino acid residues from SEQ ID NO:2 are of particular utility in constructing eSPGL-1-Ig chimeras: amino acid residues 19-43; amino acid residues 19-60; amino acid residues 19-105; and amino acid residues 19-132.

Because of the importance of post-translational modifications in non-equus PSGL/P-selectin binding, it is further envisioned that the recombinant ePSGL-1-Ig polypeptides described herein may be expressed in cell lines capable of appropriate post-translational modifications. The cell lines described in Example 3 above provide examples of suitable host cell lines and are the preferred host cells for expression of the ePSGL-1-Ig constructs, particularly the CHO(C2GnT+ Fuc-TVII) cell line.

Example 5

Determination of Equine P-selectin Binding Activity for Soluble ePSGL-1 Forms

Figure 7:
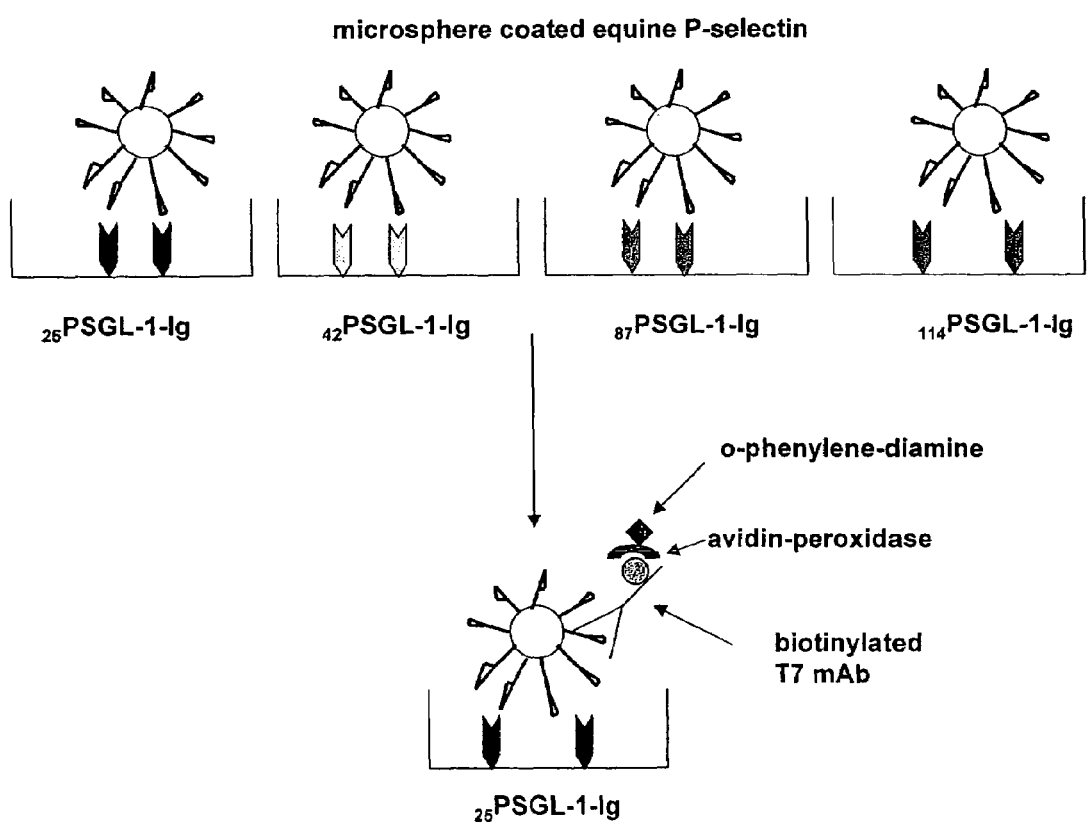
FIG. 7. Illustration of assay to determine equine PSGL-1 binding domain activity toward equine P-selectin by cell-microsphere binding assay.

A series of plasmids encoding various lengths of ePSGL-1 amino terminus which contain ePSGL-1 binding domain are constructed and expressed in CHO cells, as described in a previous example. As depicted in FIG. 7, conditioned medium is collected from the CHO cells and coated onto microtiter plates. Microspheres coated with equine P-selectin are added to the microtiter wells and unbound microspheres are then removed by washing. Microsphere bound to ePSGL-1 are then recognized upon addition of biotinylated T7 mAb, recognizing the equine P-selectin protein. Avidin-peroxidase is added with o-phenylene-diamine (0.125 wt./ vol. %) as a substrate and absorbance at 450 nm is determined using a Multiskan RC reader (ThermoLabsystems, Finland). By comparing the relative absorbance obtained for each construct versus control, the relative binding affinity for soluble ePSGL-1 forms can be obtained.

Example 6

Figure 8:
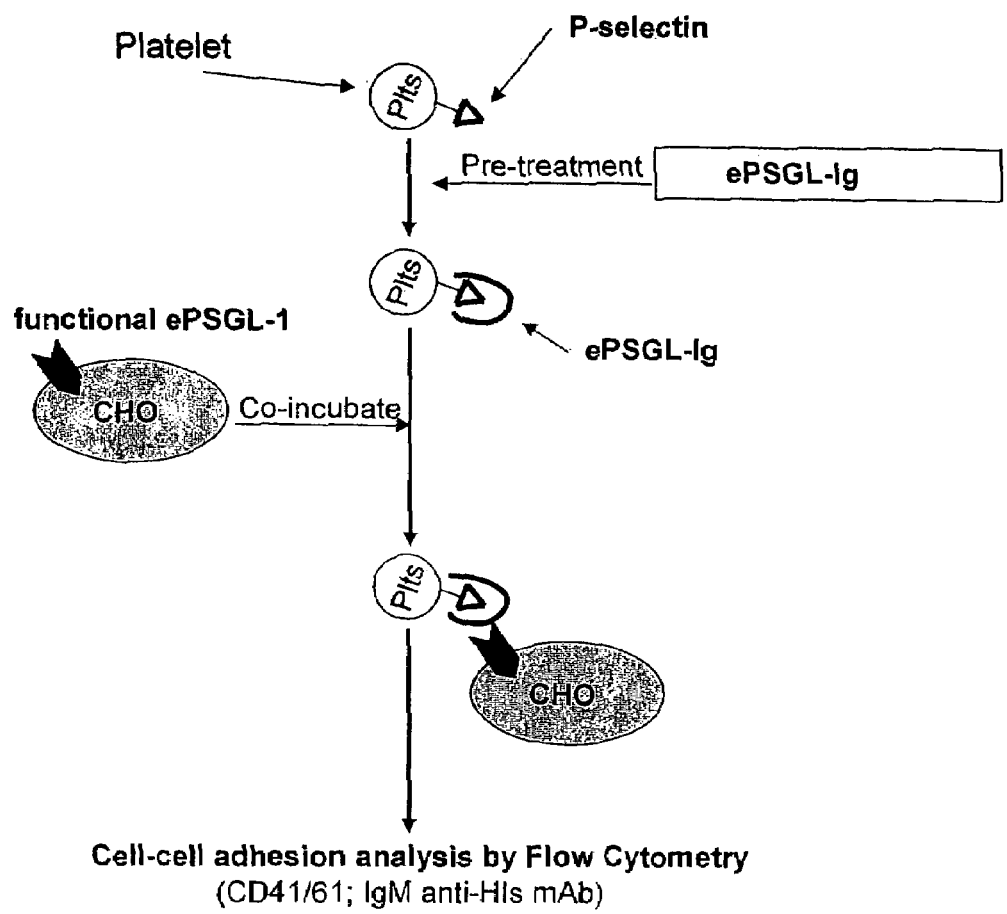
FIG. 8. Schematic illustration of assay to measure ePSGL-1-Ig modulation of cell/cell adhesion.

Capabilities of ePSGL-1 Soluble Forms to Modulate Cell-Cell Adhesion And Intracellular Signaling Reference is now made to FIG. 8 in which platelets expressing equine P-selectin is pretreated with an ePSGL-1 fusion protein according to the invention. Following this pretreatment, a CHO cell expressing functional membrane bound ePSGL-1 is co-incubated with the platelet. Flow cytometry is then carried out using CD/41/61; IgM anti-Hls mAb to determine the percentage of platelets adhering to the ePSGL-1 expressing cells.

Figure 9:
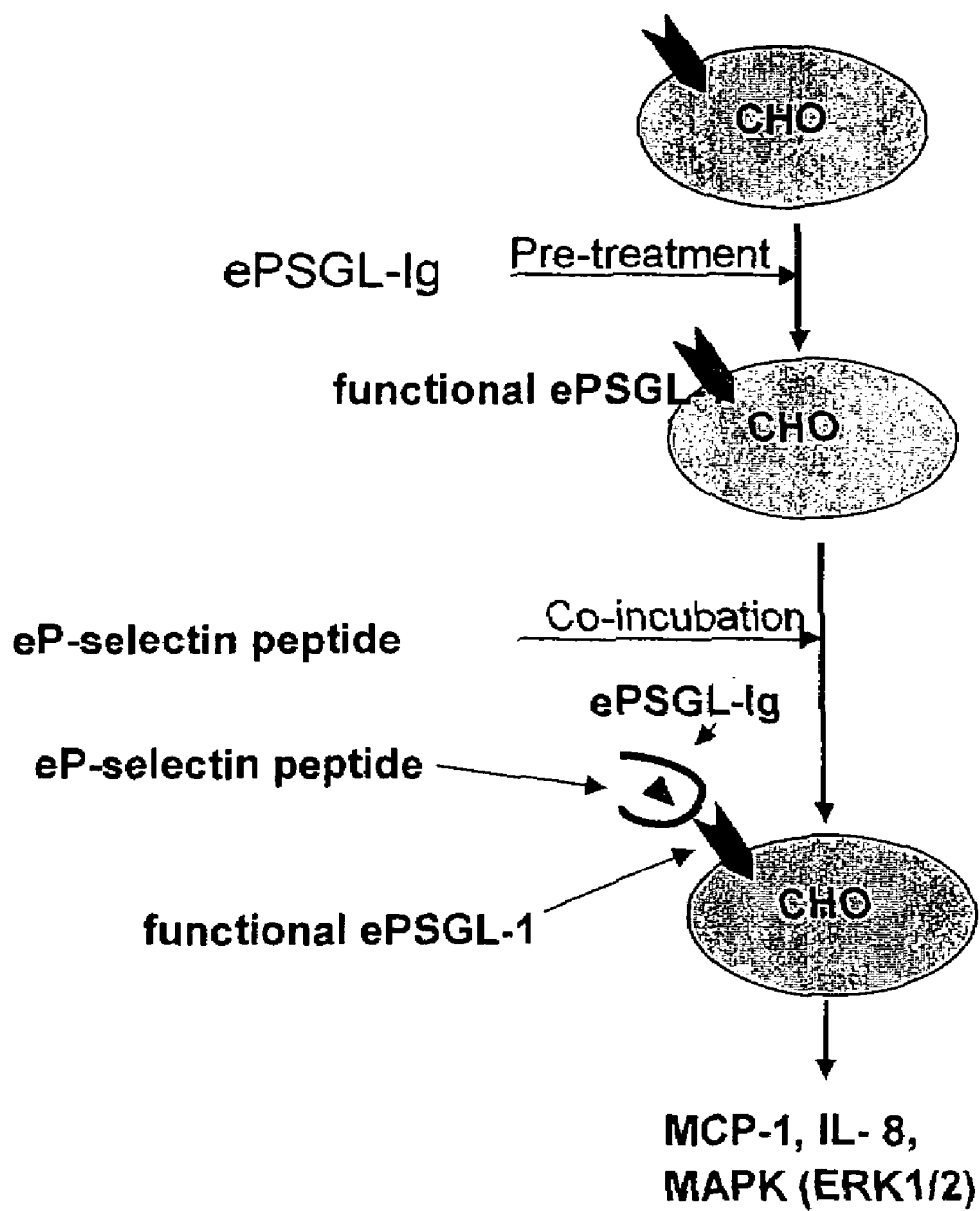
FIG. 9. Schematic illustration of assay to measure ePSGL-1-Ig modulation of cell signaling.

In FIG. 9, an assay to determine the effect of an ePSGL-1-Ig protein on ePSGL-1 intracellular signaling is depicted. A suitable cell expressing functional ePSGL is incubated with an equine P-selectin fragment capable of binding ePSGL-1. This incubation is carried out with or without the presence of the ePSGL-1-Ig protein. The levels of certain downstream targets of PSGL signaling including MAPK (ERK½) and MCP-1, IL-8 are then quantified by, for example, standard western blot and/or real time PCR procedures.

Those skilled in the art will recognize, or be able to ascertain using no more then routine experimentation, numerous equivalents to the specific polypeptides, nucleic acids, methods, assays and reagents described herein. Such equivalents are considered to be within the scope of this invention and encompassed by the following claims.

IV. REFERENCES

1. Afshar-Kharghan V, Diz-Kücükkaya R, Ludwig E H, Marian A J, López J A (2001) Human polymorphism of P-selectin glycoprotein ligand 1 attributable to variable numbers of tandem decameric repeats in the mucinlike region. Blood 97, 3306-3307
2. Bundgaard J R, Vuust J, Rehfeld J F (1997) New consensus features for Tyrosine O-Sulfation determined by mutational analysis. J Biol Chem 272, 21700-21705
3. Cummings R D (1999) Structure and function of the selectin ligand PSGL-1. Brazilian Journal of Medical and Biological Research 32, 519-528
4. Epperson T K, Patel K D, McEver R P, Cummings R D (2000) Noncovalent association of P-selectin glycoprotein ligand-1 and minimal determinants for binding to P-selectin. J Biol Chem 275, 7839-7853
5. Hicks A E R, Leppanen A, Cummings R D, McEver R P, Hellewell P G, Norman K E (2002) Glycosulfopeptides modeled on P-selectin glycoprotein ligand 1 inhibit P-selectin-dependent leukocyte rolling in vivo. FASEB J 15, 1461-1462.
6. Lalko C C, Deppe E, Ulatowski D, Lutgen A, Hart A P, Patton E A, Lunn D P, Suresh M, Darien B J (2003) Equine platelet CD62P (P-selectin) expression: a phenotypic and morphologic study. Vet Immunology and Immunopathology 91, 119-134
7. Leppanen A, White S P, Helin J, McEver R P, Cummings R D (2000) Binding of glycosulfopeptides to P-selectin required stereospecific contributions of individual tyrosine sulfate and sugar residues. J Biol Chem 275, 39569-39578
8. Li JX, Ramachandran V, McDaniel J M, Nguyen K N, Cummings R D, McEver R (2003) N-terminal residues in murine P-selectin glycoprotein ligand-1 required for binding to murine P-selectin. Blood 101,552-559
9. Li F, Erickson H P, James J A, Moore K L, Cummings R D, McEver R P (1996) Visualization of P-selectin glycoprotein ligand-1 as a highly extended molecule and mapping of protein epitopes for monoclonal antibodies. J Biol Chem 271, 6342-6348
10. Lasky L A (1995) Selectin-carbohydrate interactions and the initiation of the inflammatory response. Annu Rev Biochem 64,113-139
11. McEver R P, Cummings R D (1997) Role of PSGL-1 binding to selectins in leukocyte recruitment. J Clin Invest 100, 485-492

12. Moore K L (1998) Structure and Function of P-Selectin Glycoprotein Ligand-1. Leukemia and Lymphoma 29, 1-15
13. Morris D D (1991) Endotoxemia in horses. J Vet Intern Med 5, 167-181
14. Rodgers S D, Camphausen R T, Hammer D A (2001) Tyrosine sulfation enhances but is not required for PSGL-1 rolling adhesion on P-selectin. Biophys J 81, 2001-2009
15. Rehemtulla A, Kaufman R J (1992) Protein processing within the secratory pathway. Curr Opin Biotechnol 3, 560-565
16. Sako D, Chang X J, Barone K M, Vachino G, White H M, Shaw G, Veldman G M, Bean K M, Ahern T J, Furie B, Cumming D A, Larsen G R (1993) Expression Cloning of a Functional Glycoprotein Ligand for P-Selectin. Cell 75, 1179-1186
17. Snapp K R, Craig R, Herron M, Nelson R D, Stoolman L M, Kansas G S (1998). Dimerization of P-selectin glycoprotein ligand-1 (PSGL-1) required for optimal recognition of P-selectin. J Cell Biol 142, 263-70
18. Somers W S, Tang J, Shaw G D, Camphausen R T (2000) Insight into the molecular basis of leukocyte tethering and rolling revealed by structures of P- and E-selectin bound to Sle(X) and PSGL-1. Cell 103,467-479
19. Weiss D J, Rashid J (1998) The sepsis-coagulant axis: A review. J Vet Intern Med 12, 317-324
20. Welch R D, Watkins J P, Taylor T S, Cohen N D, Cater G K (1992) Disseminated intravascular coagulation associated with colic in 23 horses (1984-1989). J Vet Inetrn Med 6, 29-35
21. Wilkins P P, McEver R P, Cummings R D. Structure of thr O-glycans on P-selectin glycoprotein ligand-1 from HL-60 cells. J Biol Chem 271, 18732-18742
22. Xia L, Ramachandran V, McDaniel J M, Nguyen K N, Cummings R D, McEver R P (2003) N-terminal residues in murine P-selectin glycoprotein ligand-1 required for binding to murine P-selectin. Blood 101:552-559

What is claimed is:

1. An isolated polypeptide comprising:

(a) the amino acid sequence set forth in SEQ ID NO:2 capable of binding equine P-selectin; or (b) a polypeptide fragment of the ePSGL-1 extracellular domain including at least residues 19-60 of the ePSGL-1 amino acid sequence set forth in SEQ ID NO:2 capable of binding equine P-selectin.

2. The isolated polypeptide according to claim 1 modified by sulfation, glycosylation, or both.

3. A composition comprising the isolated polypeptide of claim 1 and a pharmaceutically-acceptable carrier.

* * * * *